(12) United States Patent
Irminger-Finger et al.

(10) Patent No.: US 11,137,402 B2
(45) Date of Patent: Oct. 5, 2021

(54) LUNG CANCER DIAGNOSIS

(71) Applicant: BARD1AG SA, Geneva (CH)

(72) Inventors: Irmgard Irminger-Finger, Geneva (CH); Maxim Pilyugin, Geneva (CH); Pierre-Alain Andre, Rolle (CH)

(73) Assignee: BARD1AG SA, Genève (CH)

( * ) Notice: Subject to any disclaimer, the term of this patent is extended or adjusted under 35 U.S.C. 154(b) by 92 days.

(21) Appl. No.: 15/035,194

(22) PCT Filed: Nov. 5, 2014

(86) PCT No.: PCT/EP2014/073834
§ 371 (c)(1),
(2) Date: May 6, 2016

(87) PCT Pub. No.: WO2015/067666
PCT Pub. Date: May 14, 2015

(65) Prior Publication Data
US 2016/0282347 A1 Sep. 29, 2016

(30) Foreign Application Priority Data

Nov. 6, 2013 (EP) .................................... 13191739

(51) Int. Cl.
*C07K 5/10* (2006.01)
*G01N 33/574* (2006.01)
*C07K 14/47* (2006.01)

(52) U.S. Cl.
CPC ....... *G01N 33/57423* (2013.01); *C07K 14/47* (2013.01)

(58) Field of Classification Search
None
See application file for complete search history.

(56) References Cited

U.S. PATENT DOCUMENTS

| 2004/0234959 A1 | 11/2004 | Gautier et al. |
| 2010/0130590 A1* | 5/2010 | Irminger-Finger .. C12Q 1/6886 514/44 A |
| 2013/0149711 A1 | 6/2013 | Irminger-Finger et al. |

FOREIGN PATENT DOCUMENTS

| WO | WO 2008/119802 | * 10/2008 | .............. C12Q 1/68 |
| WO | 2012/023112 A2 | 2/2012 | |
| WO | 2012/038932 A2 | 3/2012 | |

OTHER PUBLICATIONS

First Office Action dated Apr. 1, 2017 issued by the State Intellectual Property Office of P.R. China in counterpart application No. 201480071075.7.
Examination Report dated May 12, 2017 issued by the European Patent Office in counterpart application No. 14808518.6.
Irminger-Finger, I. et al., "Abstract B44:Development of a serum test for the detection of lung cancer based on oncogenic BARD1 isoform expression," Clinical Cancer Research, vol. 18, No. 3, Supplement, Feb. 1, 2012, p. 844, 1 page.
Irminger-Finger, I. et al., "Cancer-associated oncogenic BARD1 isoforms: From biomarker expression studies to development of a blood test for early detection of lung cancer," European Respiratory Journal, vol. 48, No. 56, Sep. 1, 2012, p. 1640, Abstract, 1 page.
Yong-Qiang, Z, et al. "BARD1: An independent predictor of survival in non-small cell lung cancer," International Journal of Cancer, vol. 131, No. 1, Jul. 1, 2012, pp. 83-94.
Cosandey,V. et al., "Construction of a Peptide Microarray for Auto-anti-body detection," Chimia International Journal for Chemistry, vol. 66, No. 10, Oct. 31, 2012, pp. 803-806.
Xin Li, et al., "Combining Multiple Serum Biomarkers in Tumor Diagnosis: A clinical assessment", Molecular and Clinical Oncology 1: 153-160, 2013.
Maxim Pilyugin, et al., "BARD1 serum autoantibodies for the detection of lung cancer", Plos One, https://doi.org/10.1371/journal.pone.0182356, Aug. 7, 2017, pp. 1-14.
Irminger-Finger, et al., Abstract #3335: "Identification of oncogenic BARD1 isoforms in lung cancer", Cellular and Molecular Biology, Cancer Research, vol. 69, Issue 9 Supplement, May 2009, pp. 1-2.

* cited by examiner

*Primary Examiner* — Mark Halvorson
(74) *Attorney, Agent, or Firm* — Rothwell, Figg, Ernst & Manbeck, P.C.

(57) ABSTRACT

The present invention relates to methods for detecting antibodies, methods for diagnosing lung cancer and kits for lung cancer diagnosis. The methods of the invention are based on a blood or serum sample of a subject. According to a preferred embodiment, the invention uses a combination of different peptides comprising an amino acid stretch of BARD1, short peptides and/or larger fragments thereof. In preferred embodiments, the methods of the invention comprise measuring the amount of autoimmune antibodies in the sample binding to each of the different peptides and applying a statistically determined assessment for making the diagnosis.

4 Claims, 7 Drawing Sheets
Specification includes a Sequence Listing.

LUNG CANCER DIAGNOSIS

TECHNICAL FIELD

The present invention relates to methods for diagnosis of lung cancer, methods for detecting lung cancer, methods for detecting antibodies, further methods and detection kits and diagnostic test kits.

PRIOR ART AND THE PROBLEM UNDERLYING THE INVENTION

Lung cancer is the leading cause of cancer death worldwide. Treatment methods other than surgery are not very efficient and lead to resistance. Thus, insights into the etiology of lung cancer and its progression are urgently needed. Colorectal cancer is another leading cause of cancer-related death and the fourth most common cancer worldwide. The survival and prognosis of colorectal cancer patients depends on the stage of the tumor at the time of diagnosis. Early stages of colorectal cancer can be curable. Unfortunately, over 57% have regional or distant spread of the disease at the time of diagnosis. Despite significant investment and advances in the management of cancer, the five-year survival is only 15% for advanced stage colorectal cancer patients.

Recently, many groups have addressed the mechanisms that drive lung cancer by comparing protein, RNA, and microRNA in tumors with healthy tissue. Besides TP53, the most frequently deleted or mutated gene in lung cancer, components of the p53-ARF pathway are also consistently deleted, mutated, or epigenetically modified. As to the colorectal cancer, the challenges are to understand the molecular basis, and to determine factors that initiate the development, and drive the progression. The molecular events involved in colorectal cancer onset and metastatic progression have only been partially clarified. Recent studies have revealed the potential use of molecular and biochemical markers in colorectal cancer to predict outcome and response to chemotherapy, like MLH1, MSH2, β-Catenin, and p53.

Molecular profiles are emerging as predictive and prognostic parameters in non-small-cell lung cancer (NSCLC), including genes involved in DNA damage repair, such as ERCC1, RRM1, and BRCA1. The up-regulated expression of the breast cancer predisposition gene, BRCA1 was proposed as prognostic and predictive marker for response to treatment in NSCLC. Concerning colorectal cancer, the studies of the BRCA1 are mainly limited in colorectal cancer risk and BRCA1 mutations. Several studies attempted to correlate BRCA1 mutations and colorectal cancer risk, but without any clear conclusions. Based on the current limited available evidence, BRCA mutation carriers should be regarded as at high risk for colorectal cancer. However the specific role of BRCA1 expression in colorectal cancer is unclear.

BRCA1 is expressed in many proliferating tissues and acts as a tumour suppressor in DNA repair pathways and cell cycle control. BRCA1 protein stability and function depend on its interaction with BARD1 (BRCA1 associated RING domain protein 1). The BRCA1-BARD1 heterodimer has E3 ubiquitin ligase activity, thus controlling the stability of key target proteins through ubiquitination. BARD1 is also involved in p53-dependent apoptosis, which is deficient in most lung cancers. BARD1 stabilizes p53 and promotes its phosphorylation, and expression of BARD1 is required for proper p53 functioning in signalling towards apoptosis. Thus, BARD1 plays a dual role in tumour suppression, as a binding partner of both BRCA1 and p53. Several studies have shown that BARD1 is upregulated during mitosis, transcriptionally by E2F and posttranslationally by phosphorylation, and importantly, that it is essential for mitosis. According to other studies, both BRCA1 and BARD1 were shown to interact with hMSH2, a gene commonly associated with hereditary nonpolyposis colorectal cancer (HNPCC) and mutations of hMSH2 appear to account for approximately 30-40% of HNPCC. Defects in the BRCA1-hMSH2 signalling process lead to increased susceptibility to tumorigenesis.

WO 98/12327 (Board of Regents, the University of Texas System) discloses several genes, identified in screening assays based upon binding to the breast cancer protein, BRCA1. One of these genes is termed BARD1, a RING protein that interacts with BRCA1 and is envisioned for use in various cancer-related diagnostic and therapeutic methods, particularly those connected with breast, ovarian and uterine cancer.

WO 2008/119802 (Université de Genève) discloses that in gynecological cancers, deletion-bearing isoforms of BARD1 are overexpressed and aberrantly localized to the cytoplasm, and their expression correlated with poor prognosis in breast and ovarian cancer. Structural analysis of these isoforms showed that they lacked the regions that interact with BRCA1 or induce apoptosis. These isoforms are specific to gynecological cancers and are termed as isoforms α, β, η, γ, ε, φ, δ and Ω.

WO 2012/023112 discloses novel isoforms of BARD1, which are specifically occurring in lung and colon cancers. Methods for detecting these isoforms are disclosed.

Due to the severity of lung cancers, there is an urgent need of providing effective methods for diagnosing lung cancers in a subject. Due to incurability of cancer in subjects being in an advanced state, there is an urgent need for providing methods that allow for early diagnosis of lung cancer. Early diagnosis significantly improves prognosis of subjects suffering from lung cancer.

It is an objective of the invention to provide methods of diagnosis that are non-invasive or that require minimal invasive procedures. A test for diagnosis that can be performed on the basis of a blood sample would be advantageous.

Another objective of the present invention is to provide a rapid, reliable, sensitive and specific test for diagnosis of lung cancer.

The present invention addresses the problems depicted above.

SUMMARY OF INVENTION

The present invention provides methods, kits and assays suitable in diagnosis of lung cancer.

In an aspect, the invention provides a method for detecting and/or measuring levels of antibodies in a blood and/or serum sample, wherein levels of antibodies that specifically bind to different peptides are measured, wherein said peptides comprise a stretch of the amino acid sequence of human BARD1 (SEQ ID NO: 42) and/or of an isoform thereof (SEQ ID NO: 43-51).

In an aspect, the invention provides a method for detecting and/or measuring levels of circulating antibodies of a mammalian subject, wherein antibodies that are specific to a number of different peptides are detected, wherein said peptides are related to BARD1 and/or comprise a fragment of an amino acid sequence in BARD1 or any one of its isoforms.

The amino acid sequence of human BARD1 (full length) is provided in the enclosed sequence listing under SEQ ID NO: 42. Isoforms of BARD1 encompass isoform α (alpha) (SEQ ID NO: 43); isoform π (pi) (SEQ ID NO: 44); isoform β (beta) (SEQ ID NO: 45); isoform κ (SEQ ID NO: 46); isoform γ (SEQ ID NO: 47); isoform λ (SEQ ID NO: 48); isoform φ (phi) (SEQ ID NO: 49); isoform ε (epsilon) (SEQ ID NO: 50); and isoform η (eta) (SEQ ID NO: 51).

In an aspect, the invention provides a method of diagnosing lung cancer by detecting levels of circulating antibodies in a mammalian subject, wherein antibodies that are specific to a number of different peptides are detected, wherein said peptides are related to BARD1 and/or comprise a fragment of an amino acid sequence in BARD1 or any one of its isoforms.

In an aspect, the present invention provides an in vitro and/or ex vivo method for measuring and/or detecting levels of circulating antibodies in a mammalian subject, the method comprising the steps of: a) determining, on the basis of a blood or serum sample taken from the subject, a parameter related to the amount of circulating serum antibodies specifically binding to different peptides comprising a stretch of the amino acid sequence of human BARD1 (SEQ ID NO: 42) and/or of an isoform thereof (SEQ ID NO: 43-51)

In an aspect, the present invention provides an in vitro and/or ex vivo method for diagnosing lung cancer in a mammalian subject, the method comprising the steps of: a) determining, on the basis of a blood or serum sample taken from the subject, a parameter related to the amount of circulating serum antibodies specifically binding to different peptides comprising a stretch of the amino acid sequence of human BARD1 (SEQ ID NO: 42) and/or of an isoform thereof (SEQ ID NO: 43-51); b) diagnosing, on the basis of the parameters obtained in the previous step, whether said subject suffers or not from lung cancer.

In an aspect, the present invention provides an in vitro and/or ex vivo method of detecting and/or measuring levels of antibodies associated with the occurrence of lung cancer, the method comprising the step: a) determining, on the basis of said blood or serum sample taken from the subject, parameters related to the amount of antibodies specifically binding different peptides comprising a stretch of the amino acid sequence of human BARD1 (SEQ ID NO: 42) and/or of an isoform thereof (SEQ ID NO: 43-51).

In an aspect, the present invention provides a method for assessing a probability and/or a risk that a subject suffers from lung cancer, the method comprising the steps of: a) determining, on the basis of a blood or serum sample taken from the subject, parameters related to the amount of antibodies specifically binding to different peptides comprising a stretch of the amino acid sequence of human BARD1 (SEQ ID NO: 42) and/or of an isoform thereof (SEQ ID NO: 43-51); assessing, from the parameters measured in step a) the probability and/or risk that said subject suffers from lung cancer.

In an aspect, the present invention provides the use of a combination of different peptides comprising a stretch of the amino acid sequence of human BARD1 (SEQ ID NO: 42) and/or of an isoform thereof (SEQ ID NO: 43-51) in an in vitro and/or ex vivo in the methods of the invention, for example in a method for lung cancer screening, monitoring, diagnosis, prognosis, prediction, recurrence, and/or in methods for enhancing the clinical efficiency of lung cancer screening, monitoring, diagnosis, prognosis, prediction and recurrence.

In an aspect, the present invention provides a method for detecting and/or determining levels of antibodies present in a blood and/or serum sample, the method comprising the steps of: Providing a blood or serum sample from a mammalian subject; Bringing the said blood or serum sample into contact with one or more surfaces and/or solid matrices where different peptides are bound to, said peptides comprising a stretch of the amino acid sequence of human BARD1 (SEQ ID NO: 42) and/or of an isoform thereof (SEQ ID NO: 43-51), wherein the contacting is under conditions sufficient for binding an antibody present in the said sample to the different peptides through antigen-antibody interactions; Removing the blood or serum sample for removing from the one or more surfaces or solid matrices any unbound antibody; Determining levels of an antigen-antibody complex bound to the said surfaces and/or matrices.

In an aspect, the present invention provides a method for diagnosing lung cancer in a mammalian subject, the method comprising the steps of: Providing a blood or serum sample from a mammalian subject; Bringing the said blood or serum sample into contact with one and/or more surfaces or solid matrices where different peptides are bound to, said peptides comprising a stretch of the amino acid sequence of human BARD1 (SEQ ID NO: 42) and/or of an isoform thereof (SEQ ID NO: 43-51), wherein the contacting is under conditions sufficient for binding an antibody present in the said sample to the different peptides through antigen-antibody interactions; Removing the blood or serum sample for removing any unbound antibody from the surfaces and/or matrices; Determining levels of an antigen-antibody complex bound to the said surfaces and/or matrices; and diagnosing, on the basis of the levels obtained in the previous step, whether said subject suffers or not from lung cancer.

In an aspect, the invention provides an in vitro and/or ex vivo method for diagnosing lung cancer in a female human subject. In a preferred embodiment, the method comprises the steps of: Determining, on the basis of a blood or serum sample taken from the female subject, parameters related to the amount of antibodies specifically binding to at least 19 different peptides, wherein said peptides are peptides comprising the amino acid sequences SEQ ID NO: 1 to SEQ ID NO: 6; SEQ ID NO: 11 to SEQ ID NO: 14; SEQ ID NO: 18 to SEQ ID NO: 21; SEQ ID NO: 26 to SEQ ID NO: 30, respectively; and, Diagnosing, on the basis of the parameters obtained in the previous step, whether said female subject suffers or not from lung cancer.

In an aspect, the invention provides an in vitro and/or ex vivo method for diagnosing lung cancer in a male human subject. In a preferred embodiment, this method comprises the steps of: Determining, on the basis of a blood or serum sample taken from the male subject, parameters related to the amount of antibodies specifically binding to at least 22 different peptides, wherein said peptides are peptides comprising the amino acid sequences SEQ ID NO: 1 to SEQ ID NO: 5; SEQ ID NO: 7; SEQ ID NO: 8; SEQ ID NO: 11 to SEQ ID NO: 13; SEQ ID NO: 15; SEQ ID NO: 18 to SEQ ID NO: 20; SEQ ID NO: 22; SEQ ID NO: 23; SEQ ID NO: 26; SEQ ID NO: 27; and SEQ ID NO: 31 to SEQ ID NO: 34, respectively; and Diagnosing, on the basis of the parameters obtained in the previous step, whether said male subject suffers or not from lung cancer.

In an aspect, the present invention provides an in vitro and/or ex vivo method for diagnosing lung cancer in a subject, the method comprising the steps of:

a) exposing a combination of different peptides to a blood or serum sample of the subject, wherein said peptides are selected from peptides comprising a stretch of the amino acid sequence of human BARD1 (SEQ ID NO: 42) or of an isoform thereof (SEQ ID NO: 43-51) and wherein said peptides have, independently a length of 4 to 300 amino acids;

determining a parameter related to the amount of antibodies in said sample binding to each of said peptides;

b) determining, from the parameter obtained in the previous step, whether said subject is diagnosed positive or negative for lung cancer.

In some aspects, the present invention provides kits for conducting the methods of the invention. Preferably, the kit comprises at least 4 different peptides.

In an aspect, the invention provides a diagnostic test kit for diagnosis of lung cancer, wherein said diagnostic test kit comprises a combination of at least 11 different peptides, each peptide comprising a stretch of the amino acid sequence of human BARD1 (SEQ ID NO: 42) and/or of an isoform thereof (SEQ ID NO: 43-51). In an embodiment, said different peptides are selected from the group of peptides comprising an amino acid sequence according to any one of SEQ ID NOs: 1 to 41.

Further aspects and preferred embodiments of the invention are defined herein below and in the appended claims. Further features and advantages of the invention will become apparent to the skilled person from the description of the preferred embodiments given below.

DETAILED DESCRIPTION OF THE PREFERRED EMBODIMENTS

Figure 1:
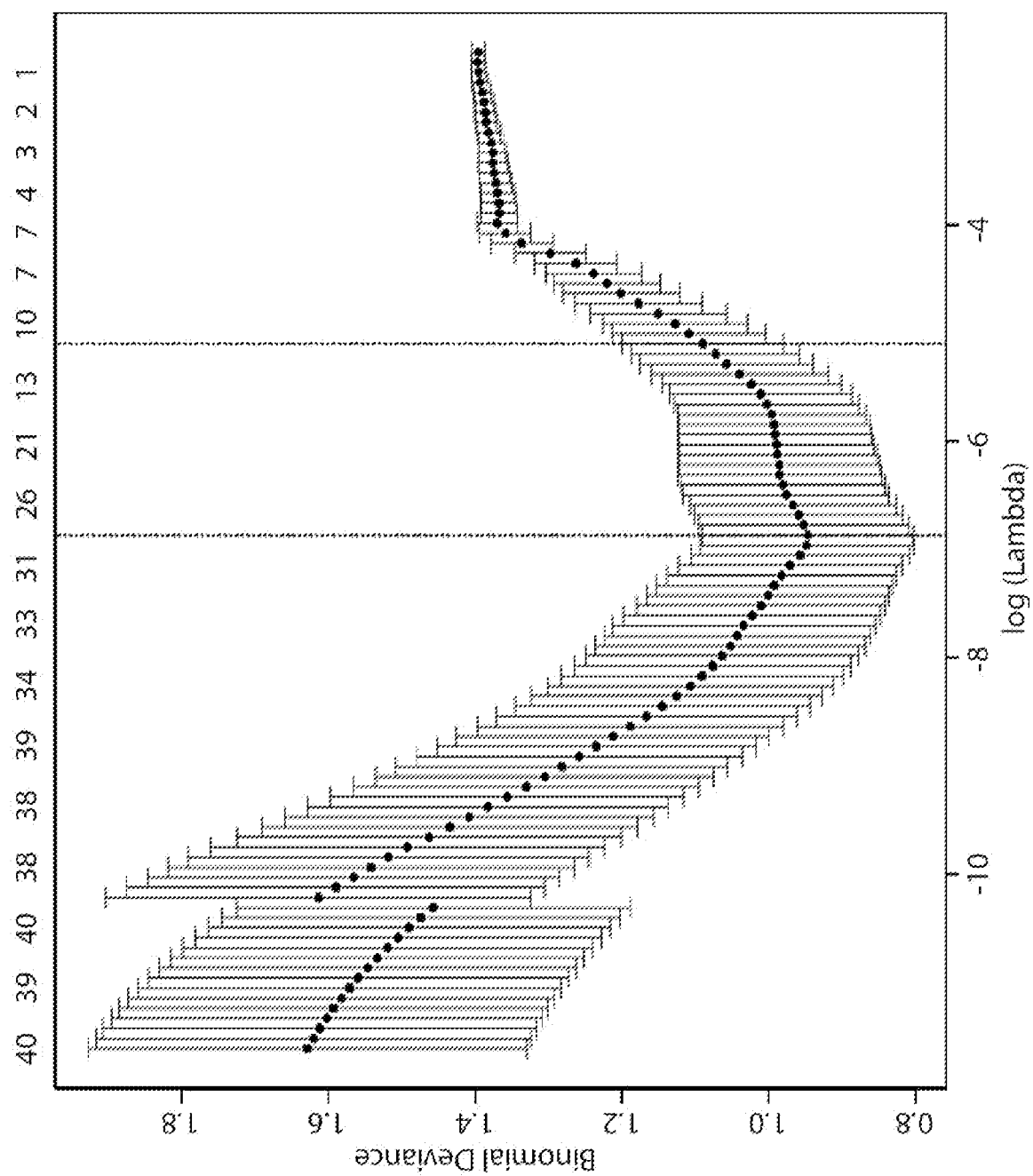
FIG. 1 shows the deviance of a fitted model (a logistic regression model here). The model shown is a measure for the quality (in means of discriminative power) of diagnostic kits for lung cancer and is used to compare different models in accordance with embodiments of the invention.

In some embodiments, the present invention relates to methods and uses of diagnosis, methods of detecting blood and/or serum antibodies of a mammalian subject, methods for detecting and/or measuring levels of antibodies associated with the occurrence of lung cancer, methods for assessing a probability and/or a risk that a subject suffers from lung cancer. The invention also relates to uses and kits.

In some embodiments, the methods of the invention comprise the step of detecting and/or measuring levels of antibodies in a blood and/or serum sample. In some embodiments, the methods of the invention comprise the step of detecting and/or measuring levels of circulating antibodies of a mammalian subject. The antibodies are preferably autoimmune antibodies.

In an embodiment, the methods of the invention are ex vivo and/or in vitro methods. The methods of the invention are preferably not conducted directly on the human or animal body. In some embodiments, the methods of the invention comprise a step of providing a blood sample. Preferably, a blood sample is taken, for example a few drops of blood are withdrawn, for example by capillary blood sampling using, for example, a blood lancet. The blood sample may also be provided by venous blood sampling (venopuncture). Preferably, the methods of the invention are conducted on the basis of a sample taken previously from a subject by routine techniques. In some embodiments, the step of blood sampling is not part of the method of the invention.

Accordingly, in some embodiments, the methods of the invention comprise a step of providing a blood or serum sample. Preferably, the blood and/or serum sample is taken from a mammalian subject.

For the purpose of the present invention, the subject is preferably a mammalian animal or a human. Most preferably, the subject is a human. According to an embodiment, the subject is a human having a history of smoking. Accordingly, the method of diagnosis is preferably specifically designed for humans that are or have been smokers. In a preferred embodiment, the method of diagnosis is preferably specifically designed for humans that have a long history of heavy smoking.

Levels of antibodies in a blood sample may be measured quantitatively and/or semi-quantitatively, for example. In some embodiments, the method of the invention comprises the step of determining a parameter related to the amount of antibodies in the sample and/or circulating antibodies. Preferably, the parameter is a numerical value, related to the amount of antibodies present in the sample. The numerical value is preferably produced in an automated process, using suitable reading and data processing equipment, as will be exemplified elsewhere in this specification.

In an embodiment, the methods of the invention comprise the step: a) determining, on the basis of a blood or serum sample taken from the subject, a parameter related to the amount of circulating serum antibodies specifically binding to different peptides comprising a stretch of the amino acid sequence of human BARD1 (SEQ ID NO: 42) and/or of an isoform thereof (SEQ ID NO: 43-51). The parameter related to the amount of serum antibodies may represent and/or correspond to the level of antibodies in said sample.

The peptides of the invention are preferably isolated and/or purified peptides. According to a preferred embodiment, the peptides are recombinant peptides. According to an embodiment, the peptides are synthetic peptides. Synthetic chemistry methods, such as solid-phase peptide synthesis, can be used to synthesize the polypeptides according to the invention. Purification of those peptides may be carried out by means of any technique known in the art of protein/peptide purification. Exemplary techniques include ion-exchange chromatography, hydrophobic interaction chromatography, and immune-affinity methods.

In an embodiment of the invention, the step of determining levels of antibodies in a blood sample and/or said step a) comprises the steps of:

1) Bringing the said blood or serum sample into contact with one or more surfaces and/or solid matrices where said different peptides are bound to, wherein the contacting is under conditions sufficient for binding an antibody present in the said sample to the different peptides through antigen-antibody interactions;

2) Removing the blood or serum sample for removing from the one or more surfaces or solid matrices any unbound antibody from the surfaces and/or matrices;

3) Determining said parameter related to the amount of circulating serum antibodies by measuring levels of an antigen-antibody complex bound to the said surfaces and/or matrices.

The expressions "solid matrix" and "solid matrices" include any solid phase support suitable for carrying out an immunoassay or a method according to the invention. It includes beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96- or a 312-well microtiter plate. In some embodiments, the "solid matrices" and/or surface refers to a carbon material or other materials suitable as electrode materials in electrochemiluminescence assays, for example.

The fixation and/or binding of the peptides according to the invention to the solid matrix, for example in the methods and kits of the invention, may be carried out by adsorption or chemical coupling to a solid phase support. Any means known in the art for immobilizing a protein or peptide to a solid support can be used. The peptides according to the invention can be either covalently or non-covalently bound to the solid matrix by techniques such as covalent bonding via an amide or ester linkage or adsorption. Peptides can be bound using binding pairs such as biotin and avidin or antibody and antigen. After the peptides are affixed to the solid matrix, the solid matrix can be incubated with a blocking solution (containing a blocking protein such as bovine serum albumin) to reduce non-specific adsorption of antibodies in a test sample to the support surface. According to one embodiment, the peptides according to the invention can be synthesized directly on the solid matrix of the kit of the invention, for example.

For the purpose of this specification, the expression "antigen-antibody complex" refers to the complex formed by the binding of the antibodies in the sample to the peptides of the invention, preferably provided on a surface and/or solid support. Therefore, "antigen-antibody complex" may also be referred to as "peptide-antibody complex" for the purpose of this specification. In said step 3), the antibodies retained on the surfaces and/or matrices are preferably those that form the antigen-antibody complex, wherein said peptides function as antigens for said antibodies.

Step 2) of removing said blood and/or serum sample is preferably conducted by washing and/or rinsing the one or more surfaces and/or solid matrices, for example with a suitable washing buffer, such as PBS. Preferably, this step does not disrupt the antigen-antibody that may have occurred in step 1).

In an embodiment, step 3) comprises the step of adding a marker molecule to the one or more surfaces or solid matrices after step 1) and/or after step 2), said marker interacting with and/or binding to the antibodies of the blood or serum sample which form the antigen-antibody complex bound to the said surfaces and/or matrices.

The marker molecule is preferably an entity that produces or can be induced to produce a signal that can be read in a signal reading step. Generally, the marker molecule associates or is associated in some way with the antibodies, in particular with the antigen-antibody complex. Therefore, the presence of the marker generally indicates the presence of the antigen-antibody complex, and, more specifically, the presence of the antibody that is specific to the peptide.

The marker may comprise an antibody or antibody fragment covalently connected to a signal-producing compound or molecule, such as a dye, etc. Alternatively, the marker may be a molecule that can be directly conjugated to the antibodies bound in the form of antigen-antibody complexes on the surfaces and/or solid matrices.

There are many types of markers available to the skilled person, such as markers producing light signals (dye), magnetic signals (e.g. magnetic beads) and radioactive signals (e.g. radioactive label for radioimmunoassay), for example.

In an embodiment, the method of the invention (for example, step a)) comprises the step of producing and/or measuring a signal that is related to the amount of antibodies in said sample binding to each of respective peptide. In an embodiment, the method comprises a step of measuring a signal that is dependent on the presence and/or quantity of an antigen-antibody complex bound to the said surfaces and/or matrices.

In preferred embodiments, the marker molecules can be induced to produce a signal that can be read with suitable reading equipment. Accordingly, in some embodiments, the method of the invention comprises a step of generating and measuring a signal that is dependent on and/or affected by the presence and/or quantity of an antigen-antibody complex bound to the said surfaces and/or matrices, wherein a quantity of said complex affects the nature, intensity and/or strength of said signal.

Depending on the marker molecule used, the skilled person will choose an appropriate method for generating the signal, such as, for example, the substrate for an enzyme in case of an ELISA, or the application of electricity in case of electrochemiluminescence, for example.

Signal reading is preferably conducted in an automated process, using suitable reading equipment. Preferably, a plate reader is used for measuring the signal. For example, if a light signal is measured, the reading equipment may comprise a light sensor, for example a photomultiplier tube and/or a camera. For example, a charge-coupled device (CCD) camera may be used.

The reading equipment generally directly calculates or determines, from the measurement of the signal, the numerical parameter that is related to the amount of antibodies in the blood sample. In case of electrochemiluminescence detection (Meso Scale Discovery, USA), SECTOR Imager 6000 and 2400 are commercially available imaging detection systems. Such apparatuses are run with suitable software that directly calculates numerical values from the signal read on the assay plates. In case of an ELISA, for example, conventional ELISA plate readers may be used for determining the numerical parameter that is related to the amount of antibodies.

In general terms, methods for conducting step a) and/or for measuring levels of antibodies in a blood sample encompass optical detection methods (e.g. ELISA), mass variation detection (e.g. surface Plasmon resonance, mass spectrometry), and electrical detection (e g impedance, spectroscopy, electrochemical) techniques.

In an embodiment, levels of antibodies in a blood sample are determined immunochemically, for example by radio-immunoassay, immunofluorescence assay or by an enzymelinked immunosorbent assay, and immunoassays based on antibodies to protein, for example.

As the skilled person will understand, the use of the word "peptide" in the singular encompasses that a plurality of the same and/or identical peptides are referred to, for example a plurality of identical peptides (in terms of sequence and/or structure) fixed on one spot of a microtiter plate.

The expression "different peptides" generally refers to peptides having different structures and/or amino acid sequences. Generally, the expression "different peptides" more specifically refers to a several pluralities or groups of peptides (a plurality of a plurality), wherein each plurality or group is characterized by the identity of the amino acid sequence and/or structure of the peptides within that plurality and/or group. On the other hand, "different peptides" are contained in different pluralities and/or groups, which are different in that the peptides they contain have a different structure and/or a different sequence. Accordingly, the expression "different peptides" is not intended to mean "different individual peptide molecules having the same amino acid sequence" for the purpose of this specification.

In accordance with an embodiment, a parameter related to the amount of antibodies is determined separately for each peptide, so as to obtain a plurality of said parameters in which each individual parameter is related to the amount of antibodies binding to one specific peptide of said different peptides.

In an embodiment, said different peptides are a combination of different peptides.

In an embodiment of the methods of the invention, the amount of antibodies is determined separately for each of said different peptides. In particular, for each of the peptides that is part of the method, kit and/or assay of the invention, a value and/or parameter is produced that is related to the amount of antibodies present in the sample. Preferably, for each of the different peptides, the level of antibodies specifically binding to the peptide is determined.

The method of the invention encompasses the use of a plurality of different peptides and measuring levels of antibodies binding to each of the different peptides.

In an embodiment, said peptides are provided in one or more wells of a microtiter plate. Preferably, in the methods of the invention, the sample of said subject is added to said one or more wells. In an embodiment, each well comprises several areas and wherein each area comprises a plurality of a specific, defined peptide selected of said combination of different peptides.

In an embodiment, all peptides of said different peptides have, independently, a length of 4 to 300, preferably 8 to 250 amino acids. In preferred embodiments, said peptides have a length of 8 to 200, more preferably 8 to 150, even more preferably 8 to 100 and most preferably 8 to 50 amino acids.

In some embodiments, the peptides are short fragments of about 6 to 30 amino acid length, for example and in other embodiments the peptides are larger fragments, having 100-300, preferably 130-260 amino acid lengths, for example. In some embodiments, the peptides used in the methods and kits of the invention comprise shorter and larger fragments and possibly fragments having a length lying in between the above ranges, for example from 30-100 amino acids.

In an embodiment, said different peptides consist of 5 to 35, preferably 11 to 30, and most preferably 17 to 28 different peptides. According to a preferred embodiment, said different peptides comprise eleven (11) or more different peptides.

In a preferred embodiment, said different peptides are selected from a group of forty-one peptides, wherein each peptide of said group of forty-one peptides comprises and or consists essentially of, respectively, one of the forty-one amino acid sequences of the group consisting of SEQ ID NO: 1 to 41. Preferably, said different peptides are a combination of different peptides, wherein said combination is formed of 41 different peptides, respectively, wherein each peptide comprises and/or consists essentially of one of the forty-one amino acid sequences of the group consisting of SEQ ID NO: 1 to 41.

For the purpose of the present specification, the expression "consists essentially of" refers to a sequence identity of at least 85%, preferably at least 90%, even more preferably at least 95%, and most preferably 97% or more. For example, "consists essentially of" refers to 98%, 99% and most preferably 99.5% of sequence identity. For the purpose of the present specification, sequence identity percentage is determined by using the basic protein blast on the internet (http_colon_//blast.ncbi.nlm.nih.gov) with preset standard parameters and database selections. This sequence comparison tool is based on algorithms detailed in the two following publications: Stephen F. Altschul, Thomas L. Madden, Alejandro A. Schffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402. Stephen F. Altschul, John C. Wootton, E. Michael Gertz, Richa Agarwala, Aleksandr Morgulis, Alejandro A. Schffer, and Yi-Kuo Yu (2005) "Protein database searches using compositionally adjusted substitution matrices", FEBS J. 272:5101-5109.

Standard parameters include the selection of blastp (protein-protein BLAST, automatic adjustment of parameters to short input sequences; expect threshold 10, word size 3, use of the matrix BLOSUM62; Gap costs: existence: 11, extension 1; conditional compositional score matrix adjustment, no filters and no masking). Sequence identity of a sequence of comparison with respect to an original sequence is reduced when, for example, any one of the compared or the original sequence lacks amino acid residues, has additional amino acid residues and/or has one or more amino acid residue substituted by another residue. Sequences having as little as 80% sequence identity with any sequence as defined herein may still provide functional, that is, are suitable as peptides in the kits and methods of the invention.

In an embodiment, the invention concerns the selection of peptides that can be used in the methods of the invention, in particular for diagnosis of lung cancer. In some embodiments, different groups of peptides are established in accordance with the invention, wherein said different peptides may be selected from one or more of these groups of peptides. Preferably, said peptides are grouped in five (5) groups, which are groups A-E.

Accordingly, in an embodiment, said different peptides comprise several groups of peptides, a group A of peptides, a group B of peptides, a group C of peptides, a group D of peptides and a group E of peptides.

In an embodiment, said group A comprises peptides comprising or consisting substantially of amino acid sequences selected from the group consisting of: SEQ ID NO: 1 (#286); SEQ ID NO: 2 (#720); SEQ ID NO: 3 (#493); SEQ ID NO: 4 (#68/524); SEQ ID NO: 5 (#140), SEQ ID NO: 6 (#139); SEQ ID NO: 7 (#349); SEQ ID NO: 8 (#117), SEQ ID NO: 9 (#5); and SEQ ID NO: 10 (#-4).

In an embodiment, said group B comprises one or more peptides comprising or consisting substantially of amino acid sequences selected from the group consisting of: SEQ ID NO: 11 (#16); SEQ ID NO: 12 (#453); and SEQ ID NO: 13 (EX4..2), SEQ ID NO: 14 (BRCT.2.), SEQ ID NO: 15 (#15), SEQ ID NO: 16 (#523); and SEQ ID NO: 17 (#109).

In an embodiment, said group C comprises one or more peptides comprising or consisting substantially of amino acid sequences selected from the group consisting of: SEQ ID NO: 18 (#117/635); SEQ ID NO: 19 (#368); SEQ ID NO: 20 (BRCT.1.), SEQ ID NO: 21 (EX4..1); SEQ ID NO: 22 (#188), SEQ ID NO: 23 (LINK), SEQ ID NO: 24 (#A21/635); and SEQ ID NO: 25 (RING).

In an embodiment, said group D comprises one or more peptides comprising or consisting substantially of amino acid sequences selected from the group consisting of: SEQ ID NO: 26 (Ank); and SEQ ID NO: 27 (#A20/122), SEQ ID NO: 28 (#54); SEQ ID NO: 29 (#48/522) and SEQ ID NO: 30 (#149); SEQ ID NO: 31 (#73); SEQ ID NO: 32 (#A-4); SEQ ID NO: 33 (#3ORF); and SEQ ID NO: 34 (#557).

In an embodiment, said group E comprises one or more peptides comprising or consisting substantially of amino acid sequences selected from the group consisting of: SEQ ID NO: 35 (#319), SEQ ID NO: 36 (#702); SEQ ID NO: 37 (#175); SEQ ID NO: 38 (#84); SEQ ID NO: 39 (#A29) SEQ ID NO: 40 (#542) and SEQ ID NO: 41 (#309).

In an embodiment, said different peptides comprise one or more peptides selected from said group A and one or more peptides selected from said any one of said groups B, C, D, and/or E.

In an embodiment, said different peptides comprise one or more peptides selected from said group A, one or more peptides selected from said group B, and one or more peptides selected from said group C, D, and/or E.

In an embodiment, said different peptides comprise one or more peptides selected from said group A, one or more peptides selected from said group B, one or more peptides selected from said group C, and one or more peptides selected from said group D and/or E.

In an embodiment, said different peptides comprise three or more peptides selected from said group A, and three or more peptides selected from said any one of said groups B, C, D, and/or E.

In an embodiment, said different peptides comprise three or more peptides selected from said group A, two or more peptides selected from said group B, and two or more peptides selected from said group C, D, and/or E.

In an embodiment, said different peptides comprise three or more peptides selected from said group A, two or more peptides selected from said group B, two or more peptides selected from said group C, and two or more peptides selected from said group D and/or E.

In an embodiment, said combination of different peptides comprises five or more peptides selected from said group A; two or more peptides selected from group B, and two or more peptides selected from group C.

In an embodiment, said combination of different peptides lacks any peptide from group E.

In an embodiment, said different peptides comprise two or more peptides comprising an amino acid sequence selected from SEQ ID NO: 1-5; one or more peptides selected from peptides SEQ ID NO: 11-13; and one or more peptides selected from SEQ ID NO: 18-20.

In an embodiment, said different peptides comprise three or more peptides comprising an amino acid sequence selected from SEQ ID NO: 1-5; two or more peptides selected from peptides SEQ ID NO: 11-13; and two or more peptides selected from SEQ ID NO: 18-20.

In an embodiment, said different peptides comprise four or more peptides comprising an amino acid sequence selected from SEQ ID NO: 1-5; three or more peptides selected from peptides SEQ ID NO: 11-13; and three or more peptides selected from SEQ ID NO: 18-20.

In an embodiment, said combination of different peptides comprises eleven (11) or more different peptides, wherein said peptides comprise, respectively, the amino acid sequences of SEQ ID NO 1-5; 11-13 and 18-20.

In an embodiment, said combination of different peptides comprises at least 10 different peptides, wherein each of said 10 peptides, respectively, comprises or consists essentially of one amino acid sequence selected from the group consisting of: SEQ ID NO: 1 to 10.

In an embodiment, said combination of different peptides comprises at least 17 different peptides, wherein each of said 17 peptides, respectively, comprises or consists essentially of one amino acid sequence selected from the group consisting of: SEQ ID NO: 1 to SEQ ID NO: 17.

In an embodiment, said combination of different peptides comprises at least 25 different peptides, wherein each of said 25 peptides, respectively, comprises or consists essentially of one amino acid sequence selected from the group consisting of: SEQ ID NO: 1 to SEQ ID NO: 25.

In an embodiment, the method of the invention is a method for diagnosing lung cancer in a human female subject. In another embodiment, the method of the invention is a method for diagnosing lung cancer in a human male subject.

If the method is specifically directed to a human female subject, the different peptides comprise preferably nineteen (19) different peptides, wherein said different peptides comprise the amino acid sequences SEQ ID NO: 1 to SEQ ID NO: 6; SEQ ID NO: 11 to SEQ ID NO: 14; SEQ ID NO: 18 to SEQ ID NO: 21; SEQ ID NO: 26 to SEQ ID NO: 30, respectively.

If the method is specifically directed to a human male subject, the different peptides comprise preferably twenty-two (22) different peptides, wherein said different peptides comprise the amino acid sequences SEQ ID NO: 1 to SEQ ID NO: 5; SEQ ID NO: 7; SEQ ID NO: 8; SEQ ID NO: 11 to SEQ ID NO: 13; SEQ ID NO: 15; SEQ ID NO: 18 to SEQ ID NO: 20; SEQ ID NO: 22; SEQ ID NO: 23; SEQ ID NO: 26; SEQ ID NO: 27; and SEQ ID NO: 31 to SEQ ID NO: 34, respectively.

In an embodiment, the method of the invention comprises a step of diagnosing whether said subject suffers or not from lung cancer. The diagnosis is preferably made on the basis of the levels of antibodies in said serum and/or blood sample and/or on the basis of the parameter related to the amount of circulating serum antibodies.

In an embodiment, the method of the invention comprises the step of calculating a test value for the subject on the basis of said parameter and/or said signal and from a statistically determined coefficient specific to each peptide. The method of the invention may comprise the step of diagnosing, by comparing said test value with a threshold value, whether said subject suffers or not from lung cancer.

In another embodiment, the method of the invention comprises the step of assessing the probability and/or a risk that a subject suffers from lung cancer by comparing said test value with one or more threshold values.

In another embodiment, the method of the invention comprises the step of enhancing the clinical efficiency of lung cancer screening, monitoring, diagnosis, prognosis, prediction and recurrence by comparing said test value with one or more threshold values. A result or outcome of said screening, monitoring, diagnosis, prognosis, prediction is then dependent on whether the test value is higher or lower than the threshold value. For example, a test value exceeding the threshold value generally indicates and/or enhances the clinical efficiency of diagnosis, prediction and/or prognosis that the subject suffers from lung cancer.

The coefficient for each peptide is preferably determined statistically. In an embodiment, the coefficient for each peptide is determined using the "Lasso-model", which is disclosed in: Ribbing J, Nyberg J, Caster O & Jonsson E N (2007) *The lasso—a novel method for predictive covariate model building in nonlinear mixed effects models. J Pharmacokinet Pharmacodyn* 34: 485-517. Specific coefficients for preferred peptides are disclosed in the examples herein below.

The levels of the antibodies and/or the parameter related to the amount of each antibody are preferably transformed into a numerical value. On the basis of the coefficient for each peptide of an assay and the numerical value determined for each peptide separately, the test value specific to a given subject is determined.

The step of diagnosis is done by comparing the test value of the subject with the predetermined threshold value. The threshold value is preferably also determined statistically using, for example, the lasso model. In particular, the threshold value can be determined statistically by using blood and/or serum samples from a number of individuals from which it is known whether or not they suffer from lung cancer. For determining the threshold value, the method used for measuring levels of antibodies in the blood and/or serum sample is preferably taken into account.

In some aspects, the present invention relates to a test kit. The expression "kit" comprises at least one peptide according to the invention or a variant thereof or a combination thereof as described herein to be coupled or already coupled to a solid matrix and optionally instructional material. Preferably, the kit comprises a solid support surface on which the different peptides are deposited and/or fixed. For example, the surface is provided on a plate, film, slides and/or wells. Preferably, the support for the peptides used in the kit is adapted to perform an antibody binding assay. In particular, the support is adapted to bind the peptides, for example covalently, and to be exposed to the blood and/or serum sample. Preferably, the support surface and/or matrix of the kit is preferably suitable to be washed for removing unbound antibody and to be exposed to a marker. The support and/or matrix comprising the peptides is preferably adapted to be read by a suitable apparatus for detecting and measuring levels and/or amounts of peptide-antibody complexes formed by non-covalent interactions.

The peptides of the kit are preferably the same as those used in the methods of the invention. Therefore, the embodiments and preferred embodiments defined elsewhere in this specification in particular with the methods of the invention also apply to the kit of the invention. This applies in particular to the selection of peptides used, but also to general peptide characteristics, such as size and number.

In an embodiment, the kit is a kit for carrying out a method according to the invention.

In an embodiment, the test kit of the invention comprises a microtiter plate comprising a plurality of wells, wherein each well comprises a plurality of areas, and wherein a plurality of one specific peptide is provided in a specific area of said well, so that each area is characteristic of a specific peptide. For example, the kit of the invention comprises a multi-spot and/or multi-array plate, such as those that are commercially available from Meso Scale Discovery, Inc., USA. For example, each well of the plate may comprise several spots, wherein each spot which is or can be coated with a peptide.

EXAMPLES

Example 1: Peptide Choice and Synthesis

Forty-one different peptides comprising SEQ ID NO: 1 to 41 were defined and selected following studies on expression of isoforms of BARD1 (SEQ ID NO: 42-51). These experiments involved siRNA-based specific repression of one isoform and confirmation of the repression of the potential translation product on Western blots, and overexpression of the isoform and confirmation of the expression of the endogenous protein of the correct size.

Studies on isoform γ (SEQ ID NO: 47), for example, confirmed that this isoform expresses a protein encoded in exons 1 to 3 (deletion of exon 4 and exons 5-11 not expressed due to stop codon in exon 5). Based on these studies, forty-one peptides were defined (SEQ ID NO: 1 to 41)

The forty-one different peptides of SEQ ID NO: 1 to 41 were synthesized by standard peptide solid phase synthesis procedures known to those skilled in the art. Purity of the peptides was at least 80%. Peptides were dissolved in stock solution in 1 mg/mL in buffer and stored in aliquots of 200 mL at −20° C. Peptides were stored in buffer carbonate, pH 9.6.

Most of the peptides of SEQ ID NO: 1 to 41 are short fragments of 8 to about 30 amino acid length. Larger fragments are SEQ ID NO: 13 (EX4..2), SEQ ID NO: 14 (BRCT.2.), SEQ ID NO: 20 (BRCT.1.), SEQ ID NO: 21 (EX4..1), SEQ ID NO: 23 (LINK), SEQ ID NO: 26 (Ank).

Example 2: Preparation of Assay Using the Peptides

The 41 peptides of Example 1 were deposited on microtiter wells using the Meso Scale MSD technology platform (Mesoscale, Md. 20850-3173, Rockeville, USA). In particular, each peptide was deposited at a determined amount on a spot of multi spot plates. Each multi spot array comprises a carbon-coated working electrode on which the peptides are deposited. For detection of antibody binding, electric stimulation results in generation of light via a sulfo-tag marker molecule (ruthenium II tris-bipyridine-(4-methylsulfonate) NSH ester. The plating of the peptides was performed by Mesoscale. Each well contains 10 different spots, so that 10 different peptides were plated in one well of a 96-well microtiter plate.

Example 3: Analysing Blood Samples of Patients and Control Subjects

Blood samples were collected from lung (n=178), colon (n=80), benign breast (n=9), malignant breast (n=14), benign ovarian (n=50), malignant ovarian (n=43), and neuroblastoma (n=20) human cancer patients and healthy controls (n=266). Gender and age was known from a majority of the subjects.

Blood samples were analyzed using the peptide-coated microtiter plates described in Example 2. Using the Meso Scale SECTOR Imager 2400 (SI2400) apparatus and the Discovery Workbench 3.0 Software, numerical values related to the amount of antibodies in the blood sample are produced.

Data analysis showed that not all patients' sera contained antibodies against the same epitopes of BARD1, but that there was a wide-spread distribution of different combinations of epitopes/peptides that were positive in cancer patients. The most distinctive and least distinctive peptides were determined from these results.

To confirm that antibodies reacted specifically with peptides presented on BARD1 isoforms, larger fragments were spotted in the same way as the shorter peptide fragments. Reactivity of serum antibodies with larger fragments confirmed the results observed with the peptides.

It was found that a combination of short peptides and larger fragments of BARD isoforms allows detecting more cancer patients.

Example 4: Statistical Analysis and Model Building

The data obtained in Example 3 were statistically analyzed. The data set consists of 379 unique samples for which at least one set of variables has been measured. For some samples, 2 or three separate measurements were made and the mean was taken. A variable is a numerical value obtained from the signal measured when exposing a blood sample to one of 40 peptides. In other words, the variable is a value related to the amount of antibodies in the sample specifically binding to one of the peptides. In total, the data set contains measurements for 40 variables, which are divided into four subsets of 10 variables each (10 different peptides are plated as 10 different sports in one well). Each plate contains measurements for peptides from one such subset, and four plates have been analyzed for each subset. The plates will be referred to by the date when they were analyzed. For some samples, only one subset of variables was measured while for others, there are measurements for several subsets. There are also some samples for which the same variables have been measured several times, on different plates. Information about gender and age are available for the majority of the studied samples. For the cancer samples more detailed diagnostic information is also provided.

Below an overview of the analysis outcome focusing on the predictive power of the test system in discriminating between control (healthy) and lung cancer blood serum samples is given. The differences in the methodology and analysis results are discussed.

The "Lasso" method was recently used to build models using different peptides selection and then compared the predictive abilities of these models (FIG. 1). When analyzing a small dataset stepwise covariate modeling procedure (SCM) may produce a covariate model that suffers from selection bias and poor predictive performance Compared to the SCM, the lasso is superior to SCM in obtaining a predictive covariate model on a small dataset or on small subgroups (Ribbing J, Nyberg J, Caster O & Jonsson E N (2007) *The lasso—a novel method for predictive covariate model building in nonlinear mixed effects models. J Pharmacokinet Pharmacodyn* 34: 485-517). Using cross-validation, the lasso provides a validation of the covariate model and does not require the user to specify a P-value for selection. This method allowed obtaining the optimal combination of oligopeptides and BARD1 fragments for discrimination between cancer and control samples. That finally leads to the selection of the best peptide combination that allow distinguish between cancer and control samples. The figure also demonstrates that increasing the number of peptides over the optimal does not produce stronger prediction power. The modeling with the use of optimal 25 variables (short peptides and larger fragments) performed for the 90 lung cancer samples versus the 94 control samples yielded AUC=0.966.

Lasso model building and feature selection was cross-validated using the R-package: glmnet. Three models have been built with 25 (SEQ ID NO: 1-25), 17 (SEQ ID NO: 1-17) or 10 (SEQ ID NO: 1-10) peptides.

FIG. 1 shows the binomial deviance of a fitted model. The number of peptides used in the model is shown on the top. The best cross-validated model is the minimum (first vertical dotted line) of this curve (26 peptides). The second dotted line is the value where the model is not significantly different (inside 1 standard error (1 se), shown as error-bars) concerning cross-validation to the models (in this case 11 peptides). Therefore the model with 17 peptides is statistically meaningful, but not the model with 10 peptides.

Figure 2:
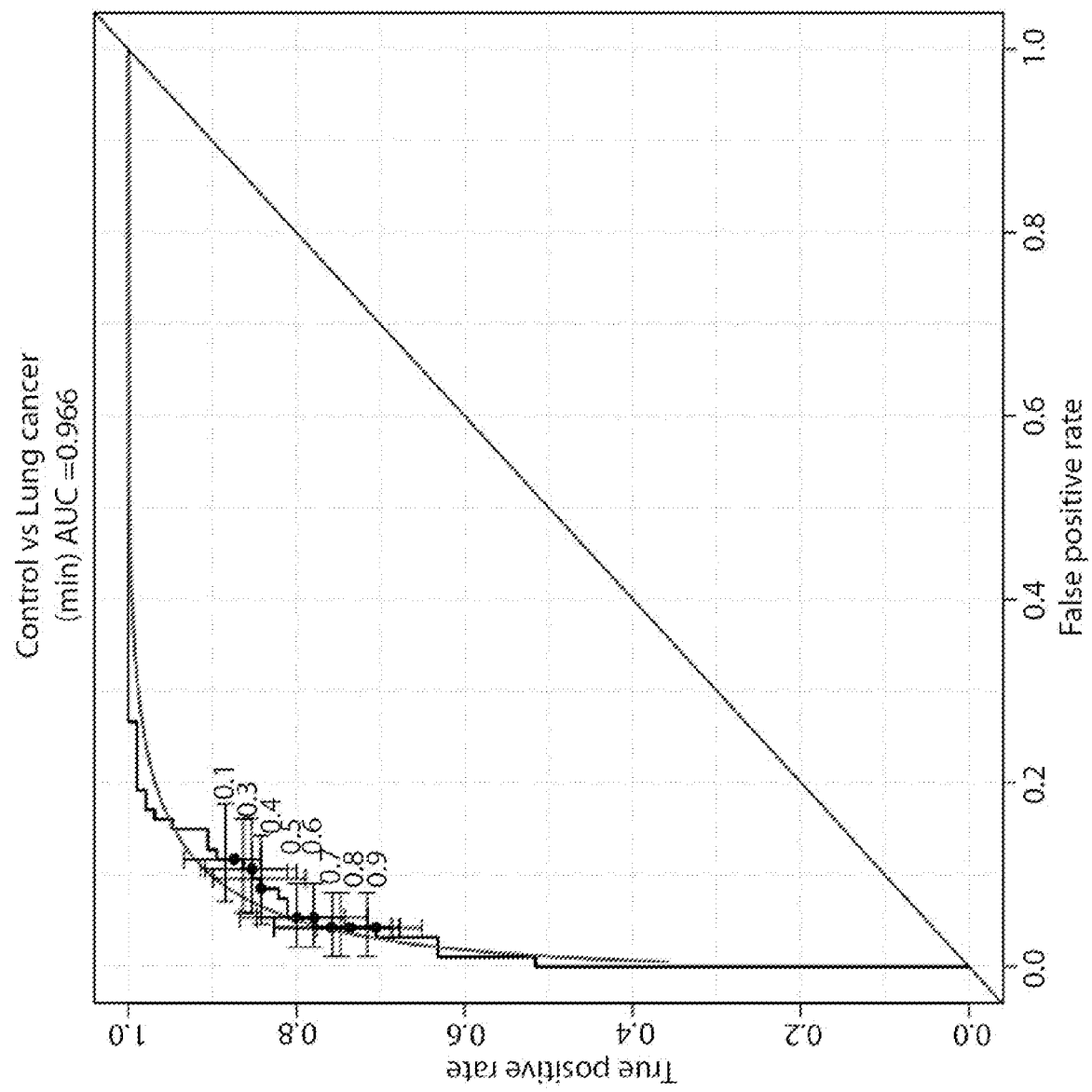
FIGS. 2 A to C show receiver operating characteristic (ROC) curves and area under the curve (AUC) values (higher is better, maximum=1) in accordance with embodiments of models of diagnostic tests in accordance with the invention. (A) Represents an optimal 25-peptide model (min), AUC=0.966, excellent discriminatory ability; (B) 17-peptide model (1se), AUC=0.927, good discriminatory ability; (C) 10-peptide model (AUC<0.828); poor discriminatory ability.
Figure 2:
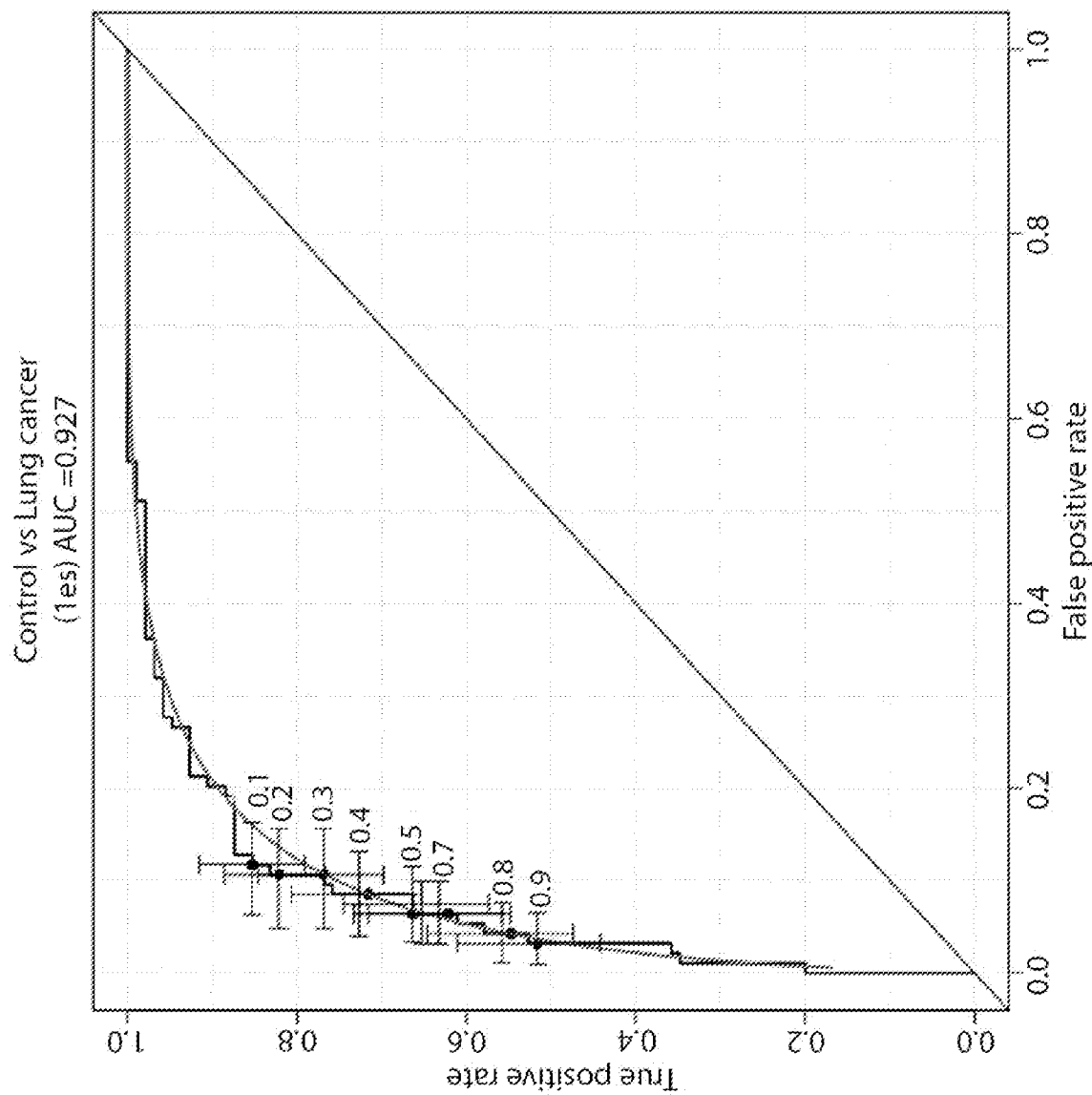
Figure 2:
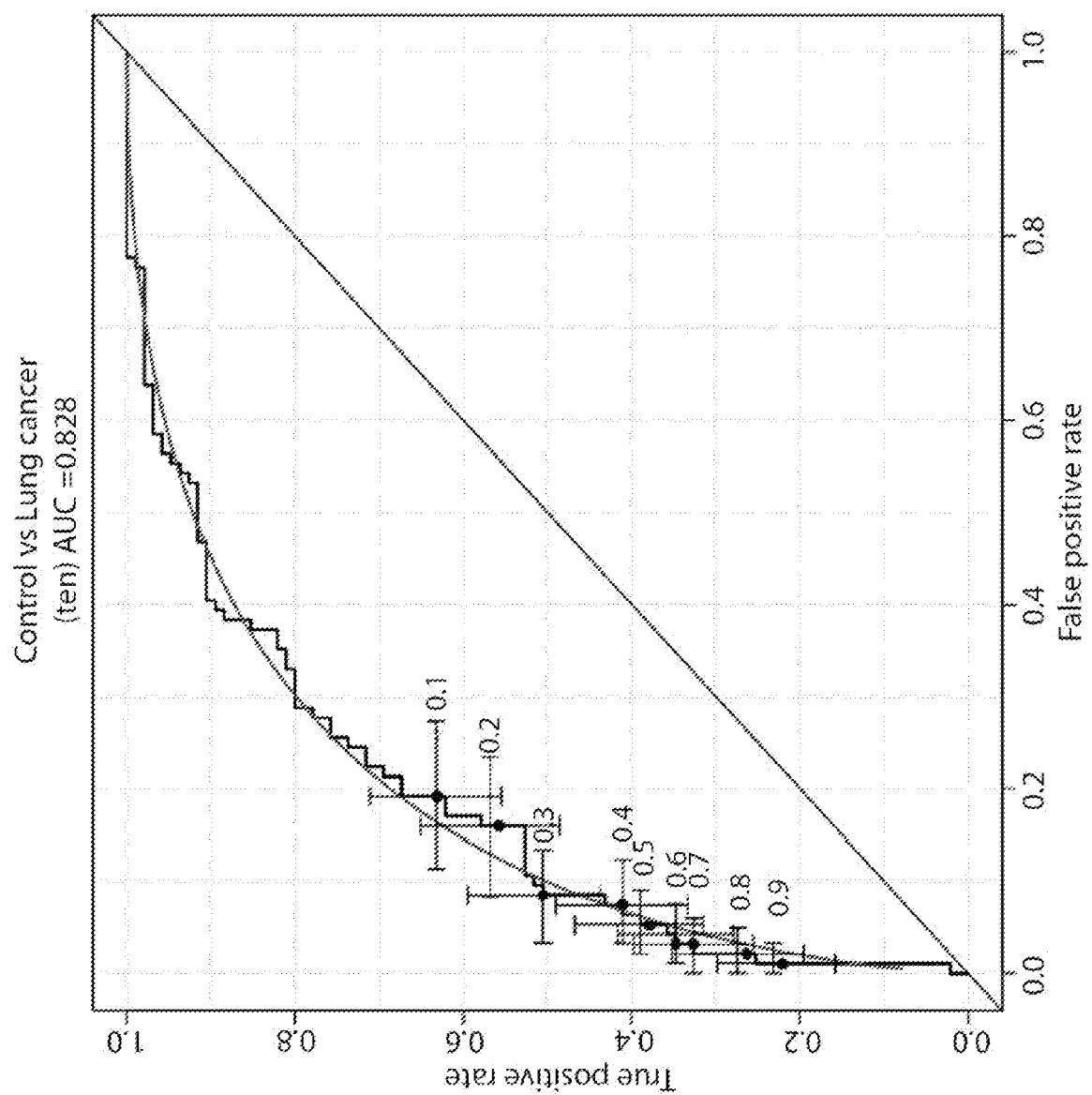

The modeling with the use of 25 variables (shorter peptides and larger fragments) (SEQ IF NO: 1-25) performed for 90 lung cancer samples versus 94 control samples yielded AUC=0.966 (FIG. 2A). These samples for the modeling were selected from the overall 379 available samples mentioned above. The modeling was also done with the aim to find the minimal set of peptides sufficient to discriminate between cancer and control with the p>0.05. For the AOC curve shown in FIG. 2B, the model with 17 peptides (SEQ IF NO: 1-17) was used, and for FIG. 3C a model with 10 peptides (SEQ IF NO: 1-10).

Figure 3:
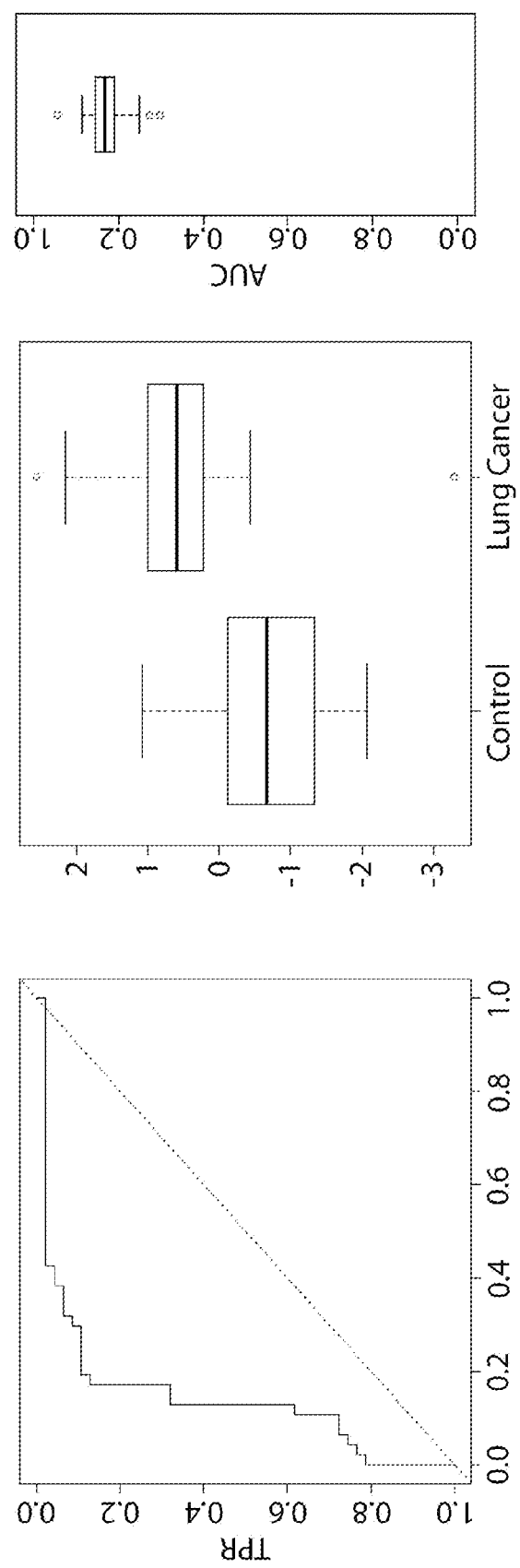
FIGS. 3 A to C illustrate the performance of support vector machine (SVM) classifiers based on 40, 30 and 10 peptides (variables), respectively. Each Figure A to C shows, from left to right, representative ROC curve; box plot showing relative signal values distribution for cancer and control samples; box plot showing the AUC value distribution in 100 modeling series (mean is ~0.83).
Figure 3:
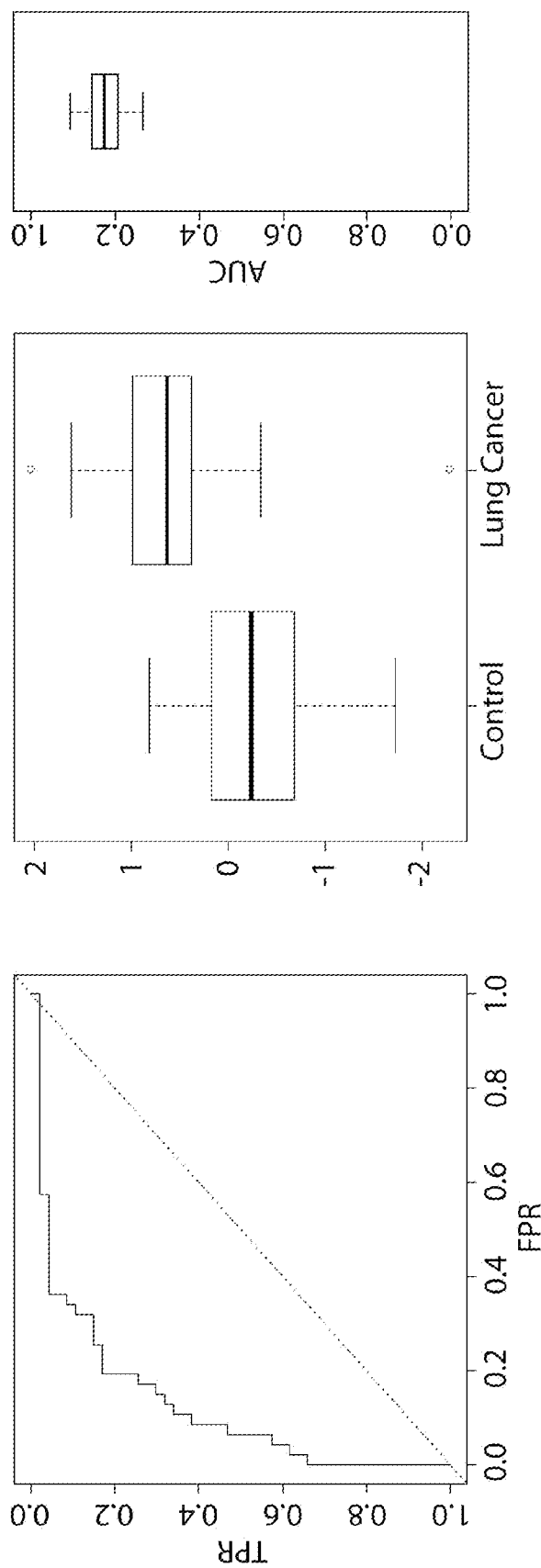
Figure 3:
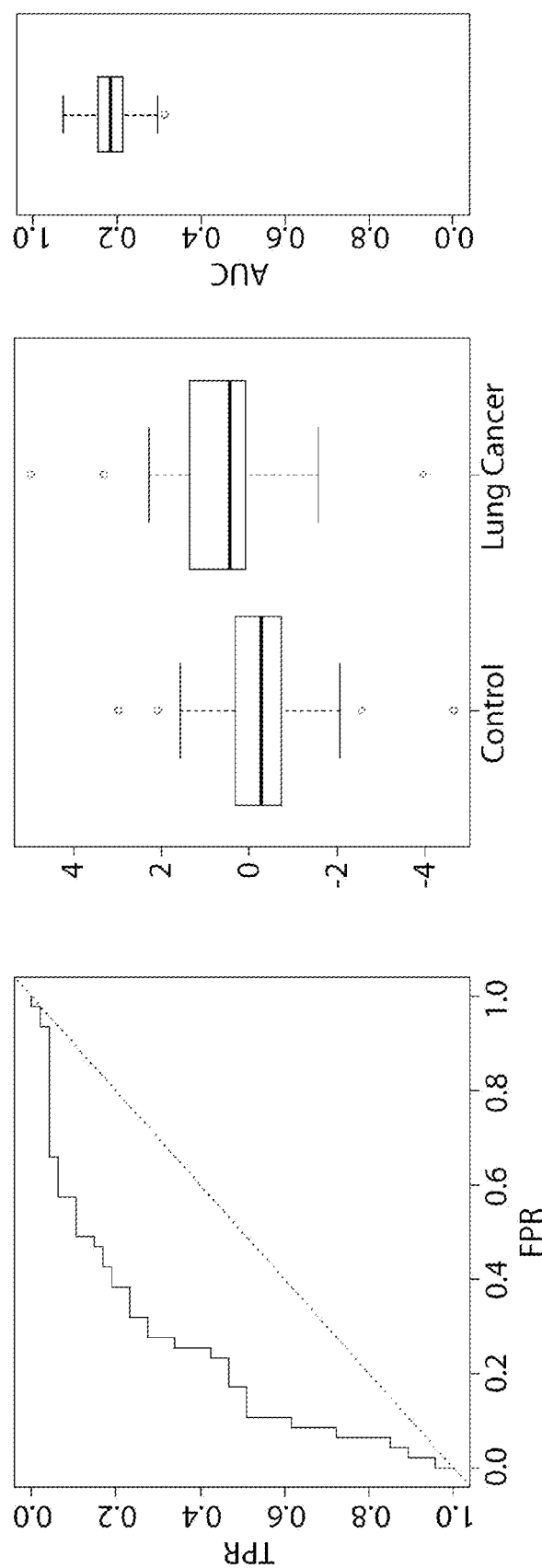

Using the Lasso method covariate model building was built with the aim of discriminating between control subjects and cancer patients. The results are shown in FIGS. 3 A to C using 40, 30 and 10 peptides in Figures A, B and C, respectively in a 100 modeling series (modeling was repeated 100 times). Each Figure A to C shows, from left to right; representative ROC curve; box plot showing relative signal values distribution for cancer and control samples; box plot showing the AUC value distribution in 100 modeling series (mean AUC is −0.83).

Example 5: Peptide Coefficients and Cutoff Value for Model with 25 Peptides

This example illustrates the calculation of a predictor value is based on coefficients attributed to each peptide as shown in Table 1 below.

Predictor=1.878155×log 10 (#16 value)−49.108×log 10 (#117 value)−16.4289×log 10 (#286 value)+24.11767×log 10 (#493 value)−3.74674×log 10 (#523 value)+39.89181×log 10 (#720 value)+3.49733×log 10 (#117/635 value)−3.21744×log 10 (#5 value)−13.1504×log 10 (#349 value)−19.78×log 10 (#453 value)+10.3537×log 10 (A21/635 value)+27.37549×log 10 (#68/524 value)−12.5612×log 10 (#15 value)−7.82582×log 10 (#109 value)+15.05732×log 10 (#139 value)+11.3804×log 10 (#140 value)+4.024697×log 10 (#188 value)−8.8073×log 10 (#368 value)+0.246625×log 10 (RING value)−0.23952×log 10 (EX4.1 value)−5.00989×log 10 (EX4.2 value)−0.17352×log 10 (LINK value)+0.726563×log 10 (BRCT1 value)+1.645815×log 10 (BRCT2 value)+3.05931×log 10 (#-4 value)−15.0948

The values, for example "#16 value" correspond to the numerical value of the parameter determined by the Meso Scale SECTOR Imager. By inserting the numerical value in the formula "Predictor" above, a predictor value is obtained, which is compared to the cutoff and/or threshold value.

TABLE 1

25 peptides model
25 Peptides MODEL

| Peptide identification (SEQ ID NO) | Peptide identification (internal) | Coefficient |
|---|---|---|
| | (Intercept) | −15.0948 |
| 11 | #16 | 1.878155 |
| 8 | #117 | −49.108 |
| 1 | #286 | −16.4289 |
| 3 | #493 | 24.11767 |
| 16 | #523 | −3.74674 |
| 2 | #720 | 39.89181 |
| 18 | #117/635 | 3.49733 |
| 9 | #5 | −3.21744 |
| 7 | #349 | −13.1504 |
| 12 | #453 | −19.78 |
| 24 | #A21/635 | 10.3537 |
| 4 | #68/524 | 27.37549 |
| 15 | #15 | −12.5612 |
| 17 | #109 | −7.82582 |
| 6 | #139 | 15.05732 |
| 5 | #140 | 11.3804 |
| 22 | #188 | 4.024697 |
| 19 | #368 | −8.8073 |
| 25 | RING | 0.246625 |
| 21 | EX4..1. | −0.23952 |
| 13 | EX4..2. | −5.00989 |
| 23 | LINK | −0.17352 |
| 20 | BRCT.1. | 0.726563 |
| 14 | BRCT.2. | 1.645815 |
| 10 | #-4 | 3.05931 |

Various cutoffs were estimated and might be used to distinguish between positive or negative. The choice of each cutoffs affect the specificity and/or sensitivity of the model. For a Maximum Specificity and Sensitivity, Cut-offs=0.08131021.

The cutoff value represents the threshold value for the outcome of the diagnostic test. If the calculated predictor is >0.08131021, the subject is diagnosed with cancer (positive test outcome). If the calculated predictor is <0.08131021, the test result is negative.

Example 6: Model for Discriminating Lung Cancer Versus Healthy in Women

Using the Lasso method described in Example 4, a model was developed for diagnosing lung cancer specifically in women. For this model, 19 peptides were found to be required to obtain a model that is statistically significant and results in excellent AUC values. The 19 different peptides are the peptides having the sequences: SEQ ID NO: 1 to SEQ ID NO: 6; SEQ ID NO: 11 to SEQ ID NO: 14; SEQ ID NO: 18 to SEQ ID NO: 21; SEQ ID NO: 26 to SEQ ID NO: 30.

Example 7: Model for Discriminating Lung Cancer Versus Healthy in Men

Using the Lasso method described in Example 4, a model was developed for diagnosing lung cancer specifically in men. For this model, 22 peptides were found to be required to obtain a model that is statistically significant and results in excellent AUC values. The 22 different peptides are the peptides having the sequences SEQ ID NO: 1 to SEQ ID NO: 5; SEQ ID NO: 7; SEQ ID NO: 8; SEQ ID NO: 11 to SEQ ID NO: 13; SEQ ID NO: 15; SEQ ID NO: 18 to SEQ ID NO: 20; SEQ ID NO: 22; SEQ ID NO: 23; SEQ ID NO: 26; SEQ ID NO: 27; and SEQ ID NO: 31 to SEQ ID NO: 34.

CONCLUSION

We have analyzed 178 lung cancer samples and 266 control samples. The dataset consists of 379 unique samples for which at least one set of variables (peptides or polypeptides) has been measured. In total, the data set contains measurements for 40 variables, which are divided into four subsets of 10 variables each.

From the raw data of the 40 peptides, an independent analysis using the "Lasso" method was performed to statistically evaluate different peptide selections. It was found that, for example, using 20 selected peptides a predictive performance of >95% (0.97 ROC) for lung cancer diagnosis is attained.

This is a highly conclusive result which gives all indications of accuracy (>95%) sufficient for predictions to the level of diagnosis of lung cancer in asymptomatic individuals. This applies in particular to individuals with a long history of heavy smoking.

The invention claimed is:

1. A diagnostic test kit for diagnosis of lung cancer, wherein said diagnostic test kit consists of a group of different peptides, wherein said group of different peptides consists of peptides consisting of amino acid sequences of SEQ ID NOs: 1-6, 11-14, 18-21 and 26-30, wherein the different peptides are affixed to a solid matrix.

2. A diagnostic test kit for diagnosis of lung cancer, wherein said diagnostic test kit consists of a group of different peptides, wherein said group of different peptides consists of peptides consisting of amino acid sequences of SEQ ID NOs:1-5, 7, 8, 11-13, 15, 18-20, 22, 23, 26, 27 and 31-34, wherein the different peptides are affixed to a solid matrix.

3. A diagnostic test kit for diagnosis of lung cancer, wherein said diagnostic test kit consists of a group of different peptides, wherein said group of different peptides consists of peptides consisting of amino acid sequences of SEQ ID NOs: 1-17, wherein the different peptides are affixed to a solid matrix.

4. A diagnostic test kit for diagnosis of lung cancer, wherein said diagnostic test kit consists of a group of different peptides, wherein said group of different peptides consists of peptides consisting of amino acid sequences of SEQ ID NOs: 1-25, wherein the different peptides are affixed to a solid matrix.

* * * * *

SEQUENCE LISTING

```
<160> NUMBER OF SEQ ID NOS: 51

<210> SEQ ID NO 1
<211> LENGTH: 15
<212> TYPE: PRT
<213> ORGANISM: Artificial Sequence
<220> FEATURE:
<223> OTHER INFORMATION: Peptide extract of human BARD1 #286
<220> FEATURE:
<221> NAME/KEY: SOURCE
<222> LOCATION: (1)..(15)
<223> OTHER INFORMATION: /mol_type="protein" /note="Peptide extract of
      human BARD1 (#286)" /organism="Artificial Sequence"

<400> SEQUENCE: 1

Ile Glu Ser Pro Asp Thr Lys Ser Arg Asn Glu Val Val Thr Cys
1               5                   10                  15
```

```
<210> SEQ ID NO 2
<211> LENGTH: 14
<212> TYPE: PRT
<213> ORGANISM: Artificial Sequence
<220> FEATURE:
<223> OTHER INFORMATION: Peptide extract of human BARD1 #720
<220> FEATURE:
<221> NAME/KEY: SOURCE
<222> LOCATION: (1)..(14)
<223> OTHER INFORMATION: /mol_type="protein" /note="Peptide extract of
      human BARD1 (#720)" /organism="Artificial Sequence"

<400> SEQUENCE: 2

Val Ala Tyr His Ala Arg Pro Asp Ser Asp Gln Arg Phe Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Peptide extract of human BARD1 #493
<220> FEATURE:
<221> NAME/KEY: SOURCE
<222> LOCATION: (1)..(15)
<223> OTHER INFORMATION: /mol_type="protein" /note="Peptide extract of
      human BARD1 (#493)" /organism="Artificial Sequence"

<400> SEQUENCE: 3

Gln Asn Asp Ser Pro Leu His Asp Ala Ala Lys Asn Gly His Cys
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Peptide extract of human BARD1 #68/524
<220> FEATURE:
<221> NAME/KEY: SOURCE
<222> LOCATION: (1)..(11)
<223> OTHER INFORMATION: /mol_type="protein" /note="Fusion of peptide
      extracts of human BARD1 (#68/524)" /organism="Artificial Sequence"

<400> SEQUENCE: 4

His Ile Phe Cys Ser Asn Ile Phe Gly Leu Cys
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Peptide extract of human BARD1 #140
<220> FEATURE:
<221> NAME/KEY: SOURCE
<222> LOCATION: (1)..(15)
<223> OTHER INFORMATION: /mol_type="protein" /note="Peptide extract of
      human BARD1 (#140)" /organism="Artificial Sequence"

<400> SEQUENCE: 5

Lys Asn Ser Ile Lys Met Trp Phe Ser Pro Arg Ser Lys Lys Cys
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Peptide extract of human BARD1 #139
<220> FEATURE:
```

```
<221> NAME/KEY: SOURCE
<222> LOCATION: (1)..(11)
<223> OTHER INFORMATION: /mol_type="protein" /note="Peptide extract of
      human BARD1 (#139)" /organism="Artificial Sequence"

<400> SEQUENCE: 6

Lys Lys Asn Ser Ile Lys Met Trp Phe Ser Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Peptide extract of human BARD1 #349
<220> FEATURE:
<221> NAME/KEY: SOURCE
<222> LOCATION: (1)..(14)
<223> OTHER INFORMATION: /mol_type="protein" /note="Peptide extract of
      human BARD1 (#349)" /organism="Artificial Sequence"

<400> SEQUENCE: 7

Lys Gln Thr Val Pro Ser Glu Asn Ile Pro Leu Pro Glu Cys
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Peptide extract of human BARD1 #117
<220> FEATURE:
<221> NAME/KEY: SOURCE
<222> LOCATION: (1)..(15)
<223> OTHER INFORMATION: /mol_type="protein" /note="Peptide extract of
      human BARD1 (#117)" /organism="Artificial Sequence"

<400> SEQUENCE: 8

Asp Asn Glu Leu Ser Asp Leu Lys Glu Asp Lys Pro Arg Lys Cys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Peptide extract of human BARD1 #5
<220> FEATURE:
<221> NAME/KEY: SOURCE
<222> LOCATION: (1)..(15)
<223> OTHER INFORMATION: /mol_type="protein" /note="Peptide extract of
      human BARD1 (#5)" /organism="Artificial Sequence"

<400> SEQUENCE: 9

Arg Gln Pro Arg Asn Arg Gln Pro Arg Ile Arg Ser Gly Asn Cys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Peptide extract of human BARD1 #-4
<220> FEATURE:
<221> NAME/KEY: SOURCE
<222> LOCATION: (1)..(15)
<223> OTHER INFORMATION: /mol_type="protein" /note="Peptide extract of
      human BARD1 (#-4)" /organism="Artificial Sequence"

<400> SEQUENCE: 10
```

```
Glu Gly Gly Thr Met Pro Asp Asn Arg Gln Pro Arg Asn Arg Cys
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: Peptide extract of human BARD1 #16
<220> FEATURE:
<221> NAME/KEY: SOURCE
<222> LOCATION: (1)..(15)
<223> OTHER INFORMATION: /mol_type="protein" /note="Pepetide extract of human BARD1 (#16)" /organism="Artificial Sequence"

<400> SEQUENCE: 11

```
Ser Gly Asn Glu Pro Arg Ser Ala Pro Ala Met Glu Pro Asp Cys
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Peptide extract of human BARD1 #453
<220> FEATURE:
<221> NAME/KEY: SOURCE
<222> LOCATION: (1)..(15)
<223> OTHER INFORMATION: /mol_type="protein" /note="Peptide extract of human BARD1 (#453)" /organism="Artificial Sequence"

<400> SEQUENCE: 12

```
Asp Pro Asn Val Lys Asp His Ala Gly Trp Thr Pro Leu His Cys
1               5                   10                  15
```

<210> SEQ ID NO 13
<211> LENGTH: 205
<212> TYPE: PRT
<213> ORGANISM: Artificial Sequence
<220> FEATURE:
<223> OTHER INFORMATION: Peptide extract of human BARD1 EX4..2
<220> FEATURE:
<221> NAME/KEY: SOURCE
<222> LOCATION: (1)..(205)
<223> OTHER INFORMATION: /mol_type="protein" /note="Peptide extract of human BARD1 (EX4..2.)" /organism="Artificial Sequence"

<400> SEQUENCE: 13

```
Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
                20                  25                  30

Thr Thr Glu Ser Glu Cys Phe Gly Ser Leu Thr Glu Val Ser Leu Pro
        35                  40                  45

Leu Ala Glu Gln Ile Glu Ser Pro Asp Thr Lys Ser Arg Asn Glu Val
    50                  55                  60

Val Thr Pro Glu Lys Val Cys Lys Asn Tyr Leu Thr Ser Lys Lys Ser
65                  70                  75                  80

Leu Pro Leu Glu Asn Asn Gly Lys Arg Gly His His Asn Arg Leu Ser
                85                  90                  95

Ser Pro Ile Ser Lys Arg Cys Arg Thr Ser Ile Leu Ser Thr Ser Gly
                100                 105                 110

Asp Phe Val Lys Gln Thr Val Pro Ser Glu Asn Ile Pro Leu Pro Glu
                115                 120                 125

Cys Ser Ser Pro Pro Ser Cys Lys Arg Lys Val Gly Gly Thr Ser Gly
```

```
                130                 135                 140
Arg Lys Asn Ser Asn Met Ser Asp Glu Phe Ile Ser Leu Ser Pro Gly
145                 150                 155                 160

Thr Pro Pro Ser Thr Leu Ser Ser Ser Tyr Arg Arg Val Met Ser
                165                 170                 175

Ser Pro Ser Ala Met Lys Leu Leu Pro Asn Met Ala Val Lys Arg Asn
            180                 185                 190

His Arg Gly Glu Thr Leu Leu His Ile Ala Ser Ile Lys
            195                 200                 205

<210> SEQ ID NO 14
<211> LENGTH: 146
<212> TYPE: PRT
<213> ORGANISM: Artificial Sequence
<220> FEATURE:
<223> OTHER INFORMATION: Peptide extract of human BARD1 BRCT.2.
<220> FEATURE:
<221> NAME/KEY: SOURCE
<222> LOCATION: (1)..(146)
<223> OTHER INFORMATION: /mol_type="protein" /note="Peptide extract of
      human BARD1 (BRCT.2.)" /organism="Artificial Sequence"

<400> SEQUENCE: 14

Met His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr Glu Gln Leu Leu Pro Lys Leu Phe Asp Gly Cys Tyr Phe Tyr Leu
                35                  40                  45

Trp Gly Thr Phe Lys His His Pro Lys Asp Asn Leu Ile Lys Leu Val
    50                  55                  60

Thr Ala Gly Gly Gly Gln Ile Leu Ser Arg Lys Pro Lys Pro Asp Ser
65                  70                  75                  80

Asp Val Thr Gln Thr Ile Asn Thr Val Ala Tyr His Ala Arg Pro Asp
                85                  90                  95

Ser Asp Gln Arg Phe Cys Thr Gln Tyr Ile Ile Tyr Glu Asp Leu Cys
            100                 105                 110

Asn Tyr His Pro Glu Arg Val Arg Gln Gly Lys Val Trp Lys Ala Pro
        115                 120                 125

Ser Ser Trp Phe Ile Asp Cys Val Met Ser Phe Glu Leu Leu Pro Leu
    130                 135                 140

Asp Ser
145

<210> SEQ ID NO 15
<211> LENGTH: 15
<212> TYPE: PRT
<213> ORGANISM: Artificial Sequence
<220> FEATURE:
<223> OTHER INFORMATION: Peptide extract of human BARD1 #15
<220> FEATURE:
<221> NAME/KEY: SOURCE
<222> LOCATION: (1)..(15)
<223> OTHER INFORMATION: /mol_type="protein" /note="Peptide extract of
      human BARD1 (#15)" /organism="Artificial Sequence"

<400> SEQUENCE: 15

Cys Gly Asn Glu Pro Arg Ser Ala Ser Ala Met Glu Pro Asp Gly
1               5                   10                  15

<210> SEQ ID NO 16
```

```
<211> LENGTH: 20
<212> TYPE: PRT
<213> ORGANISM: Artificial Sequence
<220> FEATURE:
<223> OTHER INFORMATION: Peptide extract of human BARD1 #523
<220> FEATURE:
<221> NAME/KEY: SOURCE
<222> LOCATION: (1)..(20)
<223> OTHER INFORMATION: /mol_type="protein" /note="Peptide extract of
      human BARD1 (#523)" /organism="Artificial Sequence"

<400> SEQUENCE: 16

Ser Asn Ile Phe Gly Leu Arg Pro Val Asp Tyr Thr Asp Asp Glu Ser
1               5                   10                  15

Met Lys Ser Cys
            20

<210> SEQ ID NO 17
<211> LENGTH: 14
<212> TYPE: PRT
<213> ORGANISM: Artificial Sequence
<220> FEATURE:
<223> OTHER INFORMATION: Peptide extract of human BARD1 #109
<220> FEATURE:
<221> NAME/KEY: SOURCE
<222> LOCATION: (1)..(14)
<223> OTHER INFORMATION: /mol_type="protein" /note="Peptide extract of
      human BARD1 (#109)" /organism="Artificial Sequence"

<400> SEQUENCE: 17

Ser Lys Leu Arg Asn Leu Leu His Asp Asn Glu Leu Ser Cys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Peptide extract of human BARD1 #117/635
<220> FEATURE:
<221> NAME/KEY: SOURCE
<222> LOCATION: (1)..(10)
<223> OTHER INFORMATION: /mol_type="protein" /note="Fusion of peptide
      extracts of human BARD1 (#117/635)" /organism="Artificial
      Sequence"

<400> SEQUENCE: 18

Asp Asn Glu Leu Ser Gly Val Lys Ala Cys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Peptide extract of human BARD1 #368
<220> FEATURE:
<221> NAME/KEY: SOURCE
<222> LOCATION: (1)..(14)
<223> OTHER INFORMATION: /mol_type="protein" /note="Peptide extract of
      human BARD1 (#368)" /organism="Artificial Sequence"

<400> SEQUENCE: 19

Cys Lys Arg Lys Val Gly Gly Thr Ser Gly Arg Lys Asn Ser
1               5                   10

<210> SEQ ID NO 20
<211> LENGTH: 246
<212> TYPE: PRT
<213> ORGANISM: Artificial Sequence
```

```
<220> FEATURE:
<223> OTHER INFORMATION: Peptide extract of human BARD1 BRCT.1.
<220> FEATURE:
<221> NAME/KEY: SOURCE
<222> LOCATION: (1)..(246)
<223> OTHER INFORMATION: /mol_type="protein" /note="Petide extract of
      human BARD1 (BRCT.1.)" /organism="Artificial Sequence"

<400> SEQUENCE: 20

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
                20                  25                  30

Thr Arg Arg Asp Gly Pro Leu Val Leu Ile Gly Ser Gly Leu Ser Ser
            35                  40                  45

Glu Gln Gln Lys Met Leu Ser Glu Leu Ala Val Ile Leu Lys Ala Lys
    50                  55                  60

Lys Tyr Thr Glu Phe Asp Ser Thr Val Thr His Val Val Val Pro Gly
65                  70                  75                  80

Asp Ala Val Gln Ser Thr Leu Lys Cys Met Leu Gly Ile Leu Asn Gly
                85                  90                  95

Cys Trp Ile Leu Lys Phe Glu Trp Val Lys Ala Cys Leu Arg Arg Lys
            100                 105                 110

Val Cys Glu Gln Glu Glu Lys Tyr Glu Ile Pro Glu Gly Pro Arg Arg
        115                 120                 125

Ser Arg Leu Asn Arg Glu Gln Leu Leu Pro Lys Leu Phe Asp Gly Cys
    130                 135                 140

Tyr Phe Tyr Leu Trp Gly Thr Phe Lys His His Pro Lys Asp Asn Leu
145                 150                 155                 160

Ile Lys Leu Val Thr Ala Gly Gly Gln Ile Leu Ser Arg Lys Pro
                165                 170                 175

Lys Pro Asp Ser Asp Val Thr Gln Thr Ile Asn Thr Val Ala Tyr His
                180                 185                 190

Ala Arg Pro Asp Ser Asp Gln Arg Phe Cys Thr Gln Tyr Ile Ile Tyr
            195                 200                 205

Glu Asp Leu Cys Asn Tyr His Pro Glu Arg Val Arg Gln Gly Lys Val
        210                 215                 220

Trp Lys Ala Pro Ser Ser Trp Phe Ile Asp Cys Val Met Ser Phe Glu
225                 230                 235                 240

Leu Leu Pro Leu Asp Ser
                245

<210> SEQ ID NO 21
<211> LENGTH: 206
<212> TYPE: PRT
<213> ORGANISM: Artificial Sequence
<220> FEATURE:
<223> OTHER INFORMATION: Peptide extract of human BARD1 EX4..1
<220> FEATURE:
<221> NAME/KEY: SOURCE
<222> LOCATION: (1)..(206)
<223> OTHER INFORMATION: /mol_type="protein" /note="Peptide extract of
      human BARD1 (EX4..1.)" /organism="Artificial Sequence"

<400> SEQUENCE: 21

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
                20                  25                  30
```

```
Thr Cys Ser Lys Leu Arg Asn Leu His Asp Asn Glu Leu Ser Asp
            35                  40                  45

Leu Lys Glu Asp Lys Pro Arg Lys Ser Leu Phe Asn Asp Ala Gly Asn
 50                  55                  60

Lys Lys Asn Ser Ile Lys Met Trp Phe Ser Pro Arg Ser Lys Val
 65                  70                  75                  80

Arg Tyr Val Val Ser Lys Ala Ser Val Gln Thr Gln Pro Ala Ile Lys
                     85                  90                  95

Lys Asp Ala Ser Ala Gln Gln Asp Ser Tyr Glu Phe Val Ser Pro Ser
                 100                 105                 110

Pro Pro Ala Asp Val Ser Glu Arg Ala Lys Lys Ala Ser Ala Arg Ser
             115                 120                 125

Gly Lys Lys Gln Lys Lys Lys Thr Leu Ala Glu Ile Asn Gln Lys Trp
         130                 135                 140

Asn Leu Glu Ala Glu Lys Glu Asp Gly Glu Phe Asp Ser Lys Glu Glu
145                 150                 155                 160

Ser Lys Gln Lys Leu Val Ser Phe Cys Ser Gln Pro Ser Val Ile Ser
                 165                 170                 175

Ser Pro Gln Ile Asn Gly Glu Ile Asp Leu Leu Ala Ser Gly Ser Leu
             180                 185                 190

Thr Glu Ser Glu Cys Phe Gly Ser Leu Thr Glu Val Ser Leu
         195                 200                 205

<210> SEQ ID NO 22
<211> LENGTH: 11
<212> TYPE: PRT
<213> ORGANISM: Artificial Sequence
<220> FEATURE:
<223> OTHER INFORMATION: Peptide extract of human BARD1 #188
<220> FEATURE:
<221> NAME/KEY: SOURCE
<222> LOCATION: (1)..(11)
<223> OTHER INFORMATION: /mol_type="protein" /note="Peptide extract of
      human BARD1 (#188)" /organism="Artificial Sequence"

<400> SEQUENCE: 22

Pro Ala Asp Val Ser Glu Arg Ala Lys Lys Cys
1               5                   10

<210> SEQ ID NO 23
<211> LENGTH: 129
<212> TYPE: PRT
<213> ORGANISM: Artificial Sequence
<220> FEATURE:
<223> OTHER INFORMATION: Peptide extract of human BARD1 LINK
<220> FEATURE:
<221> NAME/KEY: SOURCE
<222> LOCATION: (1)..(129)
<223> OTHER INFORMATION: /mol_type="protein" /note="Peptide extract oh
      human BARD1 (LINK)" /organism="Artificial Sequence"

<400> SEQUENCE: 23

Met His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
             20                  25                  30

Thr His Val Asp Ile Val Lys Leu Leu Ser Tyr Gly Ala Ser Arg
             35                  40                  45

Asn Ala Val Asn Ile Phe Gly Leu Arg Pro Val Asp Tyr Thr Asp Asp
 50                  55                  60

Glu Ser Met Lys Ser Leu Leu Leu Leu Pro Glu Lys Asn Glu Ser Ser
```

```
65                  70                  75                  80
Ser Ala Ser His Cys Ser Val Met Asn Thr Gly Gln Arg Arg Asp Gly
                85                  90                  95

Pro Leu Val Leu Ile Gly Ser Gly Leu Ser Ser Glu Gln Gln Lys Met
               100                 105                 110

Leu Ser Glu Leu Ala Val Ile Leu Lys Ala Lys Lys Tyr Thr Glu Phe
           115                 120                 125

Asp

<210> SEQ ID NO 24
<211> LENGTH: 8
<212> TYPE: PRT
<213> ORGANISM: Artificial Sequence
<220> FEATURE:
<223> OTHER INFORMATION: Peptide extract of human BARD1 #A21/635
<220> FEATURE:
<221> NAME/KEY: SOURCE
<222> LOCATION: (1)..(8)
<223> OTHER INFORMATION: /mol_type="protein" /note="Fusion of peptide
      extracts of human BARD1 (#A21/635)" /organism="Artificial
      Sequence"

<400> SEQUENCE: 24

Ala Ala Arg Val Gly Val Lys Ala
1               5

<210> SEQ ID NO 25
<211> LENGTH: 154
<212> TYPE: PRT
<213> ORGANISM: Artificial Sequence
<220> FEATURE:
<223> OTHER INFORMATION: Peptide extract of human BARD1 RING
<220> FEATURE:
<221> NAME/KEY: SOURCE
<222> LOCATION: (1)..(154)
<223> OTHER INFORMATION: /mol_type="protein" /note="Peptide extract of
      human BARD1 (RING)" /organism="Artificial Sequence"

<400> SEQUENCE: 25

Met His His His His His Gly Lys Pro Ile Pro Asn Pro Leu Leu
1               5                  10                  15

Gly Leu Asp Ser Thr Glu Asn Leu Tyr Phe Gln Gly Ile Asp Pro Phe
               20                  25                  30

Thr Met Pro Asp Asn Arg Gln Pro Arg Asn Arg Gln Pro Arg Ile Arg
           35                  40                  45

Ser Gly Asn Glu Pro Arg Ser Ala Pro Ala Met Glu Pro Asp Gly Arg
       50                  55                  60

Gly Ala Trp Ala His Ser Arg Ala Ala Leu Asp Arg Leu Glu Lys Leu
65                  70                  75                  80

Leu Arg Cys Ser Arg Cys Thr Asn Ile Leu Arg Glu Pro Val Cys Leu
                85                  90                  95

Gly Gly Cys Glu His Ile Phe Cys Ser Asn Cys Val Ser Asp Cys Ile
               100                 105                 110

Gly Thr Gly Cys Pro Val Cys Tyr Thr Pro Ala Trp Ile Gln Asp Leu
           115                 120                 125

Lys Ile Asn Arg Gln Leu Asp Ser Met Ile Gln Leu Cys Ser Lys Leu
       130                 135                 140

Arg Asn Leu Leu His Asp Asn Glu Leu Ser
145                 150

<210> SEQ ID NO 26
```

```
<211> LENGTH: 174
<212> TYPE: PRT
<213> ORGANISM: Artificial Sequence
<220> FEATURE:
<223> OTHER INFORMATION: Peptide extract of human BARD1 Ank
<220> FEATURE:
<221> NAME/KEY: SOURCE
<222> LOCATION: (1)..(174)
<223> OTHER INFORMATION: /mol_type="protein" /note="Peptide extract of
      human BARD1 (Ank)" /organism="Artificial Sequence"

<400> SEQUENCE: 26

Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr Asn His Arg Gly Glu Thr Leu Leu His Ile Ala Ser Ile Lys Gly
        35                  40                  45

Asp Ile Pro Ser Val Glu Tyr Leu Leu Gln Asn Gly Ser Asp Pro Asn
    50                  55                  60

Val Lys Asp His Ala Gly Trp Thr Pro Leu His Glu Ala Cys Asn His
65                  70                  75                  80

Gly His Leu Lys Val Val Glu Leu Leu Leu Gln His Lys Ala Leu Val
                85                  90                  95

Asn Thr Thr Gly Tyr Gln Asn Asp Ser Pro Leu His Asp Ala Ala Lys
            100                 105                 110

Asn Gly His Val Asp Ile Val Lys Leu Leu Leu Ser Tyr Gly Ala Ser
        115                 120                 125

Arg Asn Ala Val Asn Ile Phe Gly Leu Arg Pro Val Asp Tyr Thr Asp
    130                 135                 140

Asp Glu Ser Met Lys Ser Leu Leu Leu Leu Pro Glu Lys Asn Glu Ser
145                 150                 155                 160

Ser Ser Ala Ser His Cys Ser Val Met Asn Thr Gly Gln Arg
                165                 170

<210> SEQ ID NO 27
<211> LENGTH: 10
<212> TYPE: PRT
<213> ORGANISM: Artificial Sequence
<220> FEATURE:
<223> OTHER INFORMATION: Peptide extract of human BARD1 #A20/122
<220> FEATURE:
<221> NAME/KEY: SOURCE
<222> LOCATION: (1)..(10)
<223> OTHER INFORMATION: /mol_type="protein" /note="Fusion of peptide
      extracts of human BARD1 (#A20/122)" /organism="Artificial
      Sequence"

<400> SEQUENCE: 27

Cys Ala Ala Arg Val Asp Leu Lys Glu Asp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Peptide extract of human BARD1 #54
<220> FEATURE:
<221> NAME/KEY: SOURCE
<222> LOCATION: (1)..(11)
<223> OTHER INFORMATION: /mol_type="protein" /note="Peptide extract of
      human BARD1 (#54)" /organism="Artificial Sequence"

<400> SEQUENCE: 28
```

Thr Asn Ile Leu Arg Glu Pro Val Cys Leu Cys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Peptide extract of human BARD1 #48/522
<220> FEATURE:
<221> NAME/KEY: SOURCE
<222> LOCATION: (1)..(11)
<223> OTHER INFORMATION: /mol_type="protein" /note="Fusion of peptide
      extracts of human BARD1 (#48/522)" /organism="Artificial Sequence"

<400> SEQUENCE: 29

Leu Arg Cys Ser Arg Cys Asn Ile Phe Gly Cys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Peptide extract of human BARD1 #149
<220> FEATURE:
<221> NAME/KEY: SOURCE
<222> LOCATION: (1)..(11)
<223> OTHER INFORMATION: /mol_type="protein" /note="Peptide extract of
      human BARD1 (#149)" /organism="Artificial Sequence"

<400> SEQUENCE: 30

Pro Arg Ser Lys Lys Val Arg Tyr Val Val Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Peptide extract of human BARD1 #73
<220> FEATURE:
<221> NAME/KEY: SOURCE
<222> LOCATION: (1)..(11)
<223> OTHER INFORMATION: /mol_type="protein" /note="paptide extract of
      human BARD1 (#73)" /organism="Artificial Sequence"

<400> SEQUENCE: 31

Asn Cys Val Ser Asp Cys Ile Gly Thr Gly Cys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Peptide extract of human BARD1 #A-4
<220> FEATURE:
<221> NAME/KEY: SOURCE
<222> LOCATION: (1)..(10)
<223> OTHER INFORMATION: /mol_type="protein" /note="Peptide extract of
      human BARD1 (#A-4)" /organism="Artificial Sequence"

<400> SEQUENCE: 32

Lys Ala Gly Arg Cys Arg Ile Ile Gly Cys
1               5                   10

<210> SEQ ID NO 33
<211> LENGTH: 21

```
<212> TYPE: PRT
<213> ORGANISM: Artificial Sequence
<220> FEATURE:
<223> OTHER INFORMATION: Peptide extract of human BARD1 #ORF
<220> FEATURE:
<221> NAME/KEY: SOURCE
<222> LOCATION: (1)..(21)
<223> OTHER INFORMATION: /mol_type="protein" /note="Peptide extract of
      human BARD1 (#3ORF)" /organism="Artificial Sequence"

<400> SEQUENCE: 33

Val Ser Met Asp Leu Ala Leu Gly His Leu Tyr Ile Leu Leu Lys Leu
1               5                   10                  15

Val Met Lys Gly Thr
            20

<210> SEQ ID NO 34
<211> LENGTH: 14
<212> TYPE: PRT
<213> ORGANISM: Artificial Sequence
<220> FEATURE:
<223> OTHER INFORMATION: Peptide extract of human BARD1 #557
<220> FEATURE:
<221> NAME/KEY: SOURCE
<222> LOCATION: (1)..(14)
<223> OTHER INFORMATION: /mol_type="protein" /note="Peptide extract of
      human BARD1 (#557)" /organism="Artificial Sequence"

<400> SEQUENCE: 34

Cys Ser Val Met Asn Thr Gly Gln Arg Arg Asp Gly Pro Leu
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Peptide extract of human BARD1 #319
<220> FEATURE:
<221> NAME/KEY: SOURCE
<222> LOCATION: (1)..(15)
<223> OTHER INFORMATION: /mol_type="protein" /note="Peptide extract of
      human BARD1 (#319)" /organism="Artificial Sequence"

<400> SEQUENCE: 35

Asn Gly Lys Arg Gly His His Asn Arg Leu Ser Ser Pro Ile Cys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Peptide extract of human BARD1 #702
<220> FEATURE:
<221> NAME/KEY: SOURCE
<222> LOCATION: (1)..(15)
<223> OTHER INFORMATION: /mol_type="protein" /note="Peptide extract of
      human BARD1 (#702)" /organism="Artificial Sequence"

<400> SEQUENCE: 36

Ile Leu Ser Arg Lys Pro Lys Pro Asp Ser Asp Val Thr Gln Cys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Peptide extract of human BARD1 #175
```

```
<220> FEATURE:
<221> NAME/KEY: SOURCE
<222> LOCATION: (1)..(15)
<223> OTHER INFORMATION: /mol_type="protein" /note="Peptide extract of
      human BARD1 (#175)" /organism="Artificial Sequence"

<400> SEQUENCE: 37

Ala Gln Gln Asp Ser Tyr Glu Phe Val Ser Pro Ser Pro Pro Cys
1               5                   10                  15

<210> SEQ ID NO 38
<211> LENGTH: 25
<212> TYPE: PRT
<213> ORGANISM: Artificial Sequence
<220> FEATURE:
<223> OTHER INFORMATION: Peptide extract of human BARD1 #84
<220> FEATURE:
<221> NAME/KEY: SOURCE
<222> LOCATION: (1)..(25)
<223> OTHER INFORMATION: /mol_type="protein" /note="Peptide extract of
      human BARD1 (#84)" /organism="Artificial Sequence"

<400> SEQUENCE: 38

Pro Val Cys Tyr Thr Pro Ala Trp Ile Gln Asp Leu Lys Ile Asn Arg
1               5                   10                  15

Gln Leu Asp Ser Met Ile Gln Leu Cys
            20                  25

<210> SEQ ID NO 39
<211> LENGTH: 13
<212> TYPE: PRT
<213> ORGANISM: Artificial Sequence
<220> FEATURE:
<223> OTHER INFORMATION: Peptide extract of human BARD1 #A29
<220> FEATURE:
<221> NAME/KEY: SOURCE
<222> LOCATION: (1)..(13)
<223> OTHER INFORMATION: /mol_type="protein" /note="Peptide extract of
      human BARD1 (#A29)" /organism="Artificial Sequence"

<400> SEQUENCE: 39

Met Val Ala Val Pro Gly Pro Thr Val Ala Pro Arg Cys
1               5                   10

<210> SEQ ID NO 40
<211> LENGTH: 19
<212> TYPE: PRT
<213> ORGANISM: Artificial Sequence
<220> FEATURE:
<223> OTHER INFORMATION: Peptide extract of human BARD1 #542
<220> FEATURE:
<221> NAME/KEY: SOURCE
<222> LOCATION: (1)..(19)
<223> OTHER INFORMATION: /mol_type="protein" /note="Peptide extract of
      human BARD1 (#542)" /organism="Artificial Sequence"

<400> SEQUENCE: 40

Leu Leu Leu Leu Pro Glu Lys Asn Glu Ser Ser Ser Ala Ser His Cys
1               5                   10                  15

Ser Val Cys

<210> SEQ ID NO 41
<211> LENGTH: 15
<212> TYPE: PRT
<213> ORGANISM: Artificial Sequence
<220> FEATURE:
<223> OTHER INFORMATION: Peptide extract of human BARD1 #309
<220> FEATURE:
<221> NAME/KEY: SOURCE
```

<222> LOCATION: (1)..(15)
<223> OTHER INFORMATION: /mol_type="protein" /note="Protein extract of
      human BARD1 (#309)" /organism="Artificial Sequence"

<400> SEQUENCE: 41

Thr Ser Lys Lys Ser Leu Pro Leu Glu Asn Asn Gly Lys Arg Cys
1               5                   10                  15

<210> SEQ ID NO 42
<211> LENGTH: 777
<212> TYPE: PRT
<213> ORGANISM: Homo sapiens

<400> SEQUENCE: 42

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
        115                 120                 125

Arg Lys Ser Leu Phe Asn Asp Ala Gly Asn Lys Lys Asn Ser Ile Lys
    130                 135                 140

Met Trp Phe Ser Pro Arg Ser Lys Lys Val Arg Tyr Val Val Ser Lys
145                 150                 155                 160

Ala Ser Val Gln Thr Gln Pro Ala Ile Lys Lys Asp Ala Ser Ala Gln
                165                 170                 175

Gln Asp Ser Tyr Glu Phe Val Ser Pro Ser Pro Ala Asp Val Ser
            180                 185                 190

Glu Arg Ala Lys Lys Ala Ser Ala Arg Ser Gly Lys Lys Gln Lys Lys
        195                 200                 205

Lys Thr Leu Ala Glu Ile Asn Gln Lys Trp Asn Leu Glu Ala Glu Lys
    210                 215                 220

Glu Asp Gly Glu Phe Asp Ser Lys Glu Glu Ser Lys Gln Lys Leu Val
225                 230                 235                 240

Ser Phe Cys Ser Gln Pro Ser Val Ile Ser Ser Pro Gln Ile Asn Gly
                245                 250                 255

Glu Ile Asp Leu Leu Ala Ser Gly Ser Leu Thr Glu Ser Glu Cys Phe
            260                 265                 270

Gly Ser Leu Thr Glu Val Ser Leu Pro Leu Ala Glu Gln Ile Glu Ser
        275                 280                 285

Pro Asp Thr Lys Ser Arg Asn Glu Val Val Thr Pro Glu Lys Val Cys
    290                 295                 300

Lys Asn Tyr Leu Thr Ser Lys Lys Ser Leu Pro Leu Glu Asn Asn Gly
305                 310                 315                 320

Lys Arg Gly His His Asn Arg Leu Ser Ser Pro Ile Ser Lys Arg Cys
                325                 330                 335

```
Arg Thr Ser Ile Leu Ser Thr Ser Gly Asp Phe Val Lys Gln Thr Val
            340                 345                 350

Pro Ser Glu Asn Ile Pro Leu Pro Glu Cys Ser Ser Pro Ser Cys
        355                 360                 365

Lys Arg Lys Val Gly Gly Thr Ser Gly Arg Lys Asn Ser Asn Met Ser
        370                 375                 380

Asp Glu Phe Ile Ser Leu Ser Pro Gly Thr Pro Pro Ser Thr Leu Ser
385                 390                 395                 400

Ser Ser Ser Tyr Arg Arg Val Met Ser Ser Pro Ser Ala Met Lys Leu
                405                 410                 415

Leu Pro Asn Met Ala Val Lys Arg Asn His Arg Gly Glu Thr Leu Leu
            420                 425                 430

His Ile Ala Ser Ile Lys Gly Asp Ile Pro Ser Val Glu Tyr Leu Leu
                435                 440                 445

Gln Asn Gly Ser Asp Pro Asn Val Lys Asp His Ala Gly Trp Thr Pro
        450                 455                 460

Leu His Glu Ala Cys Asn His Gly His Leu Lys Val Val Glu Leu Leu
465                 470                 475                 480

Leu Gln His Lys Ala Leu Val Asn Thr Thr Gly Tyr Gln Asn Asp Ser
                485                 490                 495

Pro Leu His Asp Ala Ala Lys Asn Gly His Val Asp Ile Val Lys Leu
        500                 505                 510

Leu Leu Ser Tyr Gly Ala Ser Arg Asn Ala Val Asn Ile Phe Gly Leu
            515                 520                 525

Arg Pro Val Asp Tyr Thr Asp Asp Glu Ser Met Lys Ser Leu Leu Leu
        530                 535                 540

Leu Pro Glu Lys Asn Glu Ser Ser Ser Ala Ser His Cys Ser Val Met
545                 550                 555                 560

Asn Thr Gly Gln Arg Arg Asp Gly Pro Leu Val Leu Ile Gly Ser Gly
                565                 570                 575

Leu Ser Ser Glu Gln Gln Lys Met Leu Ser Glu Leu Ala Val Ile Leu
            580                 585                 590

Lys Ala Lys Lys Tyr Thr Glu Phe Asp Ser Thr Val Thr His Val Val
        595                 600                 605

Val Pro Gly Asp Ala Val Gln Ser Thr Leu Lys Cys Met Leu Gly Ile
        610                 615                 620

Leu Asn Gly Cys Trp Ile Leu Lys Phe Glu Trp Val Lys Ala Cys Leu
625                 630                 635                 640

Arg Arg Lys Val Cys Glu Gln Glu Glu Lys Tyr Glu Ile Pro Glu Gly
                645                 650                 655

Pro Arg Arg Ser Arg Leu Asn Arg Glu Gln Leu Leu Pro Lys Leu Phe
        660                 665                 670

Asp Gly Cys Tyr Phe Tyr Leu Trp Gly Thr Phe Lys His His Pro Lys
        675                 680                 685

Asp Asn Leu Ile Lys Leu Val Thr Ala Gly Gly Gln Ile Leu Ser
            690                 695                 700

Arg Lys Pro Lys Pro Asp Ser Asp Val Thr Gln Thr Ile Asn Thr Val
705                 710                 715                 720

Ala Tyr His Ala Arg Pro Asp Ser Asp Gln Arg Phe Cys Thr Gln Tyr
                725                 730                 735

Ile Ile Tyr Glu Asp Leu Cys Asn Tyr His Pro Glu Arg Val Arg Gln
            740                 745                 750
```

```
Gly Lys Val Trp Lys Ala Pro Ser Ser Trp Phe Ile Asp Cys Val Met
            755                 760                 765

Ser Phe Glu Leu Leu Pro Leu Asp Ser
            770                 775

<210> SEQ ID NO 43
<211> LENGTH: 758
<212> TYPE: PRT
<213> ORGANISM: Homo sapiens

<400> SEQUENCE: 43

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Asn Cys Val Ser Asp Cys Ile Gly Thr Gly Cys
    50                  55                  60

Pro Val Cys Tyr Thr Pro Ala Trp Ile Gln Asp Leu Lys Ile Asn Arg
65                  70                  75                  80

Gln Leu Asp Ser Met Ile Gln Leu Cys Ser Lys Leu Arg Asn Leu Leu
                85                  90                  95

His Asp Asn Glu Leu Ser Asp Leu Lys Glu Asp Lys Pro Arg Lys Ser
            100                 105                 110

Leu Phe Asn Asp Ala Gly Asn Lys Lys Asn Ser Ile Lys Met Trp Phe
        115                 120                 125

Ser Pro Arg Ser Lys Lys Val Arg Tyr Val Val Ser Lys Ala Ser Val
    130                 135                 140

Gln Thr Gln Pro Ala Ile Lys Lys Asp Ala Ser Ala Gln Gln Asp Ser
145                 150                 155                 160

Tyr Glu Phe Val Ser Pro Ser Pro Ala Asp Val Ser Glu Arg Ala
                165                 170                 175

Lys Lys Ala Ser Ala Arg Ser Gly Lys Lys Gln Lys Lys Lys Thr Leu
            180                 185                 190

Ala Glu Ile Asn Gln Lys Trp Asn Leu Glu Ala Glu Lys Glu Asp Gly
        195                 200                 205

Glu Phe Asp Ser Lys Glu Ser Lys Gln Lys Leu Val Ser Phe Cys
    210                 215                 220

Ser Gln Pro Ser Val Ile Ser Ser Pro Gln Ile Asn Gly Glu Ile Asp
225                 230                 235                 240

Leu Leu Ala Ser Gly Ser Leu Thr Glu Ser Glu Cys Phe Gly Ser Leu
                245                 250                 255

Thr Glu Val Ser Leu Pro Leu Ala Glu Gln Ile Glu Ser Pro Asp Thr
            260                 265                 270

Lys Ser Arg Asn Glu Val Val Thr Pro Glu Lys Val Cys Lys Asn Tyr
        275                 280                 285

Leu Thr Ser Lys Lys Ser Leu Pro Leu Glu Asn Asn Gly Lys Arg Gly
    290                 295                 300

His His Asn Arg Leu Ser Ser Pro Ile Ser Lys Arg Cys Arg Thr Ser
305                 310                 315                 320

Ile Leu Ser Thr Ser Gly Asp Phe Val Lys Gln Thr Val Pro Ser Glu
                325                 330                 335

Asn Ile Pro Leu Pro Glu Cys Ser Ser Pro Ser Cys Lys Arg Lys
            340                 345                 350
```

```
Val Gly Gly Thr Ser Gly Arg Lys Asn Ser Asn Met Ser Asp Glu Phe
            355                 360                 365

Ile Ser Leu Ser Pro Gly Thr Pro Ser Thr Leu Ser Ser Ser Ser
370                 375                 380

Tyr Arg Arg Val Met Ser Ser Pro Ser Ala Met Lys Leu Leu Pro Asn
385                 390                 395                 400

Met Ala Val Lys Arg Asn His Arg Gly Glu Thr Leu Leu His Ile Ala
                405                 410                 415

Ser Ile Lys Gly Asp Ile Pro Ser Val Glu Tyr Leu Leu Gln Asn Gly
                420                 425                 430

Ser Asp Pro Asn Val Lys Asp His Ala Gly Trp Thr Pro Leu His Glu
            435                 440                 445

Ala Cys Asn His Gly His Leu Lys Val Val Glu Leu Leu Leu Gln His
        450                 455                 460

Lys Ala Leu Val Asn Thr Thr Gly Tyr Gln Asn Asp Ser Pro Leu His
465                 470                 475                 480

Asp Ala Ala Lys Asn Gly His Val Asp Ile Val Lys Leu Leu Leu Ser
                485                 490                 495

Tyr Gly Ala Ser Arg Asn Ala Val Asn Ile Phe Gly Leu Arg Pro Val
            500                 505                 510

Asp Tyr Thr Asp Asp Glu Ser Met Lys Ser Leu Leu Leu Leu Pro Glu
            515                 520                 525

Lys Asn Glu Ser Ser Ser Ala Ser His Cys Ser Val Met Asn Thr Gly
            530                 535                 540

Gln Arg Arg Asp Gly Pro Leu Val Leu Ile Gly Ser Gly Leu Ser Ser
545                 550                 555                 560

Glu Gln Gln Lys Met Leu Ser Glu Leu Ala Val Ile Leu Lys Ala Lys
                565                 570                 575

Lys Tyr Thr Glu Phe Asp Ser Thr Val Thr His Val Val Pro Gly
            580                 585                 590

Asp Ala Val Gln Ser Thr Leu Lys Cys Met Leu Gly Ile Leu Asn Gly
            595                 600                 605

Cys Trp Ile Leu Lys Phe Glu Trp Val Lys Ala Cys Leu Arg Arg Lys
        610                 615                 620

Val Cys Glu Gln Glu Glu Lys Tyr Glu Ile Pro Glu Gly Pro Arg Arg
625                 630                 635                 640

Ser Arg Leu Asn Arg Glu Gln Leu Leu Pro Lys Leu Phe Asp Gly Cys
                645                 650                 655

Tyr Phe Tyr Leu Trp Gly Thr Phe Lys His His Pro Lys Asp Asn Leu
            660                 665                 670

Ile Lys Leu Val Thr Ala Gly Gly Gln Ile Leu Ser Arg Lys Pro
            675                 680                 685

Lys Pro Asp Ser Asp Val Thr Gln Thr Ile Asn Thr Val Ala Tyr His
690                 695                 700

Ala Arg Pro Asp Ser Asp Gln Arg Phe Cys Thr Gln Tyr Ile Ile Tyr
705                 710                 715                 720

Glu Asp Leu Cys Asn Tyr His Pro Glu Arg Val Arg Gln Gly Lys Val
                725                 730                 735

Trp Lys Ala Pro Ser Ser Trp Phe Ile Asp Cys Val Met Ser Phe Glu
            740                 745                 750

Leu Leu Pro Leu Asp Ser
            755
```

<210> SEQ ID NO 44
<211> LENGTH: 641
<212> TYPE: PRT
<213> ORGANISM: Homo sapiens

<400> SEQUENCE: 44

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
                20                  25                  30

Ala Trp Ala His Ser Arg Ala Ala Leu Asp Arg Leu Glu Lys Leu Leu
            35                  40                  45

Arg Cys Ser Arg Cys Thr Asn Ile Leu Arg Glu Pro Val Cys Leu Gly
        50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Asp Leu Lys Glu Asp Lys Pro
        115                 120                 125

Arg Lys Ser Leu Phe Asn Asp Ala Gly Asn Lys Lys Asn Ser Ile Lys
    130                 135                 140

Met Trp Phe Ser Pro Arg Ser Lys Lys Val Arg Tyr Val Val Ser Lys
145                 150                 155                 160

Ala Ser Val Gln Thr Gln Pro Ala Ile Lys Lys Asp Ala Ser Ala Gln
                165                 170                 175

Gln Asp Ser Tyr Glu Phe Val Ser Pro Ser Pro Ala Asp Val Ser
            180                 185                 190

Glu Arg Ala Lys Lys Ala Ser Ala Arg Ser Gly Lys Lys Gln Lys Lys
        195                 200                 205

Lys Thr Leu Ala Glu Ile Asn Gln Lys Trp Asn Leu Glu Ala Glu Lys
    210                 215                 220

Glu Asp Gly Glu Phe Asp Ser Lys Glu Ser Lys Gln Lys Leu Val
225                 230                 235                 240

Ser Phe Cys Ser Gln Pro Ser Val Ile Ser Pro Gln Ile Asn Gly
                245                 250                 255

Glu Ile Asp Leu Leu Ala Ser Gly Ser Leu Thr Glu Ser Glu Cys Phe
            260                 265                 270

Gly Ser Leu Thr Glu Val Ser Leu Pro Leu Ala Glu Gln Ile Glu Ser
        275                 280                 285

Pro Asp Thr Lys Ser Arg Asn Glu Val Val Thr Pro Glu Lys Gly Asp
    290                 295                 300

Ile Pro Ser Val Glu Tyr Leu Leu Gln Asn Gly Ser Asp Pro Asn Val
305                 310                 315                 320

Lys Asp His Ala Gly Trp Thr Pro Leu His Glu Ala Cys Asn His Gly
                325                 330                 335

His Leu Lys Val Val Glu Leu Leu Gln His Lys Ala Leu Val Asn
            340                 345                 350

Thr Thr Gly Tyr Gln Asn Asp Ser Pro Leu His Asp Ala Ala Lys Asn
        355                 360                 365

Gly His Val Asp Ile Val Lys Leu Leu Leu Ser Tyr Gly Ala Ser Arg
    370                 375                 380

-continued

```
Asn Ala Val Asn Ile Phe Gly Leu Arg Pro Val Asp Tyr Thr Asp Asp
385                 390                 395                 400

Glu Ser Met Lys Ser Leu Leu Leu Pro Glu Lys Asn Glu Ser Ser
            405                 410                 415

Ser Ala Ser His Cys Ser Val Met Asn Thr Gly Gln Arg Arg Asp Gly
            420                 425                 430

Pro Leu Val Leu Ile Gly Ser Gly Leu Ser Ser Glu Gln Gln Lys Met
            435                 440                 445

Leu Ser Glu Leu Ala Val Ile Leu Lys Ala Lys Lys Tyr Thr Glu Phe
450                 455                 460

Asp Ser Thr Val Thr His Val Val Pro Gly Asp Ala Val Gln Ser
465                 470                 475                 480

Thr Leu Lys Cys Met Leu Gly Ile Leu Asn Gly Cys Trp Ile Leu Lys
            485                 490                 495

Phe Glu Trp Val Lys Ala Cys Leu Arg Arg Lys Val Cys Glu Gln Glu
            500                 505                 510

Glu Lys Tyr Glu Ile Pro Glu Gly Pro Arg Arg Ser Arg Leu Asn Arg
            515                 520                 525

Glu Gln Leu Leu Pro Lys Leu Phe Asp Gly Cys Tyr Phe Tyr Leu Trp
            530                 535                 540

Gly Thr Phe Lys His His Pro Lys Asp Asn Leu Ile Lys Leu Val Thr
545                 550                 555                 560

Ala Gly Gly Gly Gln Ile Leu Ser Arg Lys Pro Lys Pro Asp Ser Asp
            565                 570                 575

Val Thr Gln Thr Ile Asn Thr Val Ala Tyr His Ala Arg Pro Asp Ser
            580                 585                 590

Asp Gln Arg Phe Cys Thr Gln Tyr Ile Ile Tyr Glu Asp Leu Cys Asn
            595                 600                 605

Tyr His Pro Glu Arg Val Arg Gln Gly Lys Val Trp Lys Ala Pro Ser
            610                 615                 620

Ser Trp Phe Ile Asp Cys Val Met Ser Phe Glu Leu Leu Pro Leu Asp
625                 630                 635                 640

Ser

<210> SEQ ID NO 45
<211> LENGTH: 680
<212> TYPE: PRT
<213> ORGANISM: Homo sapiens

<400> SEQUENCE: 45

Met Val Ala Val Pro Gly Pro Thr Val Ala Pro Arg Ser Thr Ala Trp
1               5                   10                  15

Arg Ser Cys Cys Ala Ala Arg Val Asp Leu Lys Glu Asp Lys Pro Arg
            20                  25                  30

Lys Ser Leu Phe Asn Asp Ala Gly Asn Lys Asn Ser Ile Lys Met
            35                  40                  45

Trp Phe Ser Pro Arg Ser Lys Lys Val Arg Tyr Val Ser Lys Ala
    50                  55                  60

Ser Val Gln Thr Gln Pro Ala Ile Lys Lys Asp Ala Ser Ala Gln Gln
65                  70                  75                  80

Asp Ser Tyr Glu Phe Val Ser Pro Ser Pro Ala Asp Val Ser Glu
                85                  90                  95

Arg Ala Lys Lys Ala Ser Ala Arg Ser Gly Lys Lys Gln Lys Lys
            100                 105                 110
```

```
Thr Leu Ala Glu Ile Asn Gln Lys Trp Asn Leu Glu Ala Glu Lys Glu
            115                 120                 125

Asp Gly Glu Phe Asp Ser Lys Glu Glu Ser Lys Gln Lys Leu Val Ser
        130                 135                 140

Phe Cys Ser Gln Pro Ser Val Ile Ser Pro Gln Ile Asn Gly Glu
145                 150                 155                 160

Ile Asp Leu Leu Ala Ser Gly Ser Leu Thr Glu Ser Glu Cys Phe Gly
                165                 170                 175

Ser Leu Thr Glu Val Ser Leu Pro Leu Ala Glu Gln Ile Glu Ser Pro
            180                 185                 190

Asp Thr Lys Ser Arg Asn Glu Val Val Thr Pro Glu Lys Val Cys Lys
        195                 200                 205

Asn Tyr Leu Thr Ser Lys Lys Ser Leu Pro Leu Glu Asn Asn Gly Lys
    210                 215                 220

Arg Gly His His Asn Arg Leu Ser Ser Pro Ile Ser Lys Arg Cys Arg
225                 230                 235                 240

Thr Ser Ile Leu Ser Thr Ser Gly Asp Phe Val Lys Gln Thr Val Pro
                245                 250                 255

Ser Glu Asn Ile Pro Leu Pro Glu Cys Ser Ser Pro Ser Cys Lys
            260                 265                 270

Arg Lys Val Gly Gly Thr Ser Gly Arg Lys Asn Ser Asn Met Ser Asp
        275                 280                 285

Glu Phe Ile Ser Leu Ser Pro Gly Thr Pro Ser Thr Leu Ser Ser
    290                 295                 300

Ser Ser Tyr Arg Arg Val Met Ser Ser Pro Ser Ala Met Lys Leu Leu
305                 310                 315                 320

Pro Asn Met Ala Val Lys Arg Asn His Arg Gly Glu Thr Leu Leu His
                325                 330                 335

Ile Ala Ser Ile Lys Gly Asp Ile Pro Ser Val Glu Tyr Leu Leu Gln
            340                 345                 350

Asn Gly Ser Asp Pro Asn Val Lys Asp His Ala Gly Trp Thr Pro Leu
        355                 360                 365

His Glu Ala Cys Asn His Gly His Leu Lys Val Glu Leu Leu Leu
    370                 375                 380

Gln His Lys Ala Leu Val Asn Thr Thr Gly Tyr Gln Asn Asp Ser Pro
385                 390                 395                 400

Leu His Asp Ala Ala Lys Asn Gly His Val Asp Ile Val Lys Leu Leu
                405                 410                 415

Leu Ser Tyr Gly Ala Ser Arg Asn Ala Val Asn Ile Phe Gly Leu Arg
            420                 425                 430

Pro Val Asp Tyr Thr Asp Asp Glu Ser Met Lys Ser Leu Leu Leu Leu
        435                 440                 445

Pro Glu Lys Asn Glu Ser Ser Ser Ala Ser His Cys Ser Val Met Asn
    450                 455                 460

Thr Gly Gln Arg Arg Asp Gly Pro Leu Val Leu Ile Gly Ser Gly Leu
465                 470                 475                 480

Ser Ser Glu Gln Gln Lys Met Leu Ser Glu Leu Ala Val Ile Leu Lys
                485                 490                 495

Ala Lys Lys Tyr Thr Glu Phe Asp Ser Thr Val Thr His Val Val Val
            500                 505                 510

Pro Gly Asp Ala Val Gln Ser Thr Leu Lys Cys Met Leu Gly Ile Leu
        515                 520                 525
```

```
Asn Gly Cys Trp Ile Leu Lys Phe Glu Trp Val Lys Ala Cys Leu Arg
    530                 535                 540

Arg Lys Val Cys Glu Gln Glu Lys Tyr Glu Ile Pro Gly Pro
545                 550                 555                 560

Arg Arg Ser Arg Leu Asn Arg Glu Gln Leu Leu Pro Lys Leu Phe Asp
                565                 570                 575

Gly Cys Tyr Phe Tyr Leu Trp Gly Thr Phe Lys His His Pro Lys Asp
                580                 585                 590

Asn Leu Ile Lys Leu Val Thr Ala Gly Gly Gln Ile Leu Ser Arg
        595                 600                 605

Lys Pro Lys Pro Asp Ser Asp Val Thr Gln Thr Ile Asn Thr Val Ala
610                 615                 620

Tyr His Ala Arg Pro Asp Ser Asp Gln Arg Phe Cys Thr Gln Tyr Ile
625                 630                 635                 640

Ile Tyr Glu Asp Leu Cys Asn Tyr His Pro Glu Arg Val Arg Gln Gly
                645                 650                 655

Lys Val Trp Lys Ala Pro Ser Ser Trp Phe Ile Asp Cys Val Met Ser
                660                 665                 670

Phe Glu Leu Leu Pro Leu Asp Ser
        675                 680

<210> SEQ ID NO 46
<211> LENGTH: 633
<212> TYPE: PRT
<213> ORGANISM: Homo sapiens

<400> SEQUENCE: 46

Met Trp Phe Ser Pro Arg Ser Lys Lys Val Arg Tyr Val Val Ser Lys
1               5                   10                  15

Ala Ser Val Gln Thr Gln Pro Ala Ile Lys Lys Asp Ala Ser Ala Gln
                20                  25                  30

Gln Asp Ser Tyr Glu Phe Val Ser Pro Ser Pro Ala Asp Val Ser
            35                  40                  45

Glu Arg Ala Lys Lys Ala Ser Ala Arg Ser Gly Lys Lys Gln Lys Lys
50                  55                  60

Lys Thr Leu Ala Glu Ile Asn Gln Lys Trp Asn Leu Glu Ala Glu Lys
65                  70                  75                  80

Glu Asp Gly Glu Phe Asp Ser Lys Glu Glu Ser Lys Gln Lys Leu Val
                85                  90                  95

Ser Phe Cys Ser Gln Pro Ser Val Ile Ser Pro Gln Ile Asn Gly
                100                 105                 110

Glu Ile Asp Leu Leu Ala Ser Gly Ser Leu Thr Glu Ser Glu Cys Phe
        115                 120                 125

Gly Ser Leu Thr Glu Val Ser Leu Pro Leu Ala Glu Gln Ile Glu Ser
    130                 135                 140

Pro Asp Thr Lys Ser Arg Asn Glu Val Val Thr Pro Glu Lys Val Cys
145                 150                 155                 160

Lys Asn Tyr Leu Thr Ser Lys Lys Ser Leu Pro Leu Glu Asn Asn Gly
                165                 170                 175

Lys Arg Gly His His Asn Arg Leu Ser Ser Pro Ile Ser Lys Arg Cys
            180                 185                 190

Arg Thr Ser Ile Leu Ser Thr Ser Gly Asp Phe Val Lys Gln Thr Val
        195                 200                 205

Pro Ser Glu Asn Ile Pro Leu Pro Glu Cys Ser Ser Pro Pro Ser Cys
    210                 215                 220
```

```
Lys Arg Lys Val Gly Gly Thr Ser Gly Arg Lys Asn Ser Asn Met Ser
225                 230                 235                 240

Asp Glu Phe Ile Ser Leu Ser Pro Gly Thr Pro Pro Ser Thr Leu Ser
                245                 250                 255

Ser Ser Ser Tyr Arg Arg Val Met Ser Ser Pro Ser Ala Met Lys Leu
            260                 265                 270

Leu Pro Asn Met Ala Val Lys Arg Asn His Arg Gly Glu Thr Leu Leu
        275                 280                 285

His Ile Ala Ser Ile Lys Gly Asp Ile Pro Ser Val Glu Tyr Leu Leu
    290                 295                 300

Gln Asn Gly Ser Asp Pro Asn Val Lys Asp His Ala Gly Trp Thr Pro
305                 310                 315                 320

Leu His Glu Ala Cys Asn His Gly His Leu Lys Val Val Glu Leu Leu
                325                 330                 335

Leu Gln His Lys Ala Leu Val Asn Thr Thr Gly Tyr Gln Asn Asp Ser
            340                 345                 350

Pro Leu His Asp Ala Ala Lys Asn Gly His Val Asp Ile Val Lys Leu
        355                 360                 365

Leu Leu Ser Tyr Gly Ala Ser Arg Asn Ala Val Asn Ile Phe Gly Leu
    370                 375                 380

Arg Pro Val Asp Tyr Thr Asp Asp Glu Ser Met Lys Ser Leu Leu Leu
385                 390                 395                 400

Leu Pro Glu Lys Asn Glu Ser Ser Ala Ser His Cys Ser Val Met
                405                 410                 415

Asn Thr Gly Gln Arg Arg Asp Gly Pro Leu Val Leu Ile Gly Ser Gly
            420                 425                 430

Leu Ser Ser Glu Gln Lys Met Leu Ser Glu Leu Ala Val Ile Leu
        435                 440                 445

Lys Ala Lys Lys Tyr Thr Glu Phe Asp Ser Thr Val Thr His Val Val
    450                 455                 460

Val Pro Gly Asp Ala Val Gln Ser Thr Leu Lys Cys Met Leu Gly Ile
465                 470                 475                 480

Leu Asn Gly Cys Trp Ile Leu Lys Phe Glu Trp Val Lys Ala Cys Leu
                485                 490                 495

Arg Arg Lys Val Cys Glu Gln Glu Lys Tyr Glu Ile Pro Glu Gly
            500                 505                 510

Pro Arg Arg Ser Arg Leu Asn Arg Glu Gln Leu Leu Pro Lys Leu Phe
        515                 520                 525

Asp Gly Cys Tyr Phe Tyr Leu Trp Gly Thr Phe Lys His His Pro Lys
    530                 535                 540

Asp Asn Leu Ile Lys Leu Val Thr Ala Gly Gly Gln Ile Leu Ser
545                 550                 555                 560

Arg Lys Pro Lys Pro Asp Ser Asp Val Thr Gln Thr Ile Asn Thr Val
                565                 570                 575

Ala Tyr His Ala Arg Pro Asp Ser Asp Gln Arg Phe Cys Thr Gln Tyr
            580                 585                 590

Ile Ile Tyr Glu Asp Leu Cys Asn Tyr His Pro Glu Arg Val Arg Gln
        595                 600                 605

Gly Lys Val Trp Lys Ala Pro Ser Ser Trp Phe Ile Asp Cys Val Met
    610                 615                 620

Ser Phe Glu Leu Leu Pro Leu Asp Ser
625                 630
```

<210> SEQ ID NO 47
<211> LENGTH: 127
<212> TYPE: PRT
<213> ORGANISM: Homo sapiens

<400> SEQUENCE: 47

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Gly Arg His Thr Phe Cys
        115                 120                 125

<210> SEQ ID NO 48
<211> LENGTH: 307
<212> TYPE: PRT
<213> ORGANISM: Homo sapiens

<400> SEQUENCE: 48

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Asn Ile Phe Gly Leu Arg Pro Val Asp Tyr Thr
    50                  55                  60

Asp Asp Glu Ser Met Lys Ser Leu Leu Leu Pro Glu Lys Asn Glu
65                  70                  75                  80

Ser Ser Ser Ala Ser His Cys Ser Val Met Asn Thr Gly Gln Arg Arg
                85                  90                  95

Asp Gly Pro Leu Val Leu Ile Gly Ser Gly Leu Ser Ser Glu Gln Gln
            100                 105                 110

Lys Met Leu Ser Glu Leu Ala Val Ile Leu Lys Ala Lys Lys Tyr Thr
        115                 120                 125

Glu Phe Asp Ser Thr Val Thr His Val Val Pro Gly Asp Ala Val
130                 135                 140

Gln Ser Thr Leu Lys Cys Met Leu Gly Ile Leu Asn Gly Cys Trp Ile
145                 150                 155                 160

Leu Lys Phe Glu Trp Val Lys Ala Cys Leu Arg Arg Lys Val Cys Glu
                165                 170                 175

Gln Glu Glu Lys Tyr Glu Ile Pro Glu Gly Pro Arg Arg Ser Arg Leu
            180                 185                 190

Asn Arg Glu Gln Leu Leu Pro Lys Leu Phe Asp Gly Cys Tyr Phe Tyr
        195                 200                 205

```
Leu Trp Gly Thr Phe Lys His His Pro Lys Asp Asn Leu Ile Lys Leu
            210                 215                 220

Val Thr Ala Gly Gly Gln Ile Leu Ser Arg Lys Pro Lys Pro Asp
225                 230                 235                 240

Ser Asp Val Thr Gln Thr Ile Asn Thr Val Ala Tyr His Ala Arg Pro
                245                 250                 255

Asp Ser Asp Gln Arg Phe Cys Thr Gln Tyr Ile Ile Tyr Glu Asp Leu
            260                 265                 270

Cys Asn Tyr His Pro Glu Arg Val Arg Gln Gly Lys Val Trp Lys Ala
            275                 280                 285

Pro Ser Ser Trp Phe Ile Asp Cys Val Met Ser Phe Glu Leu Leu Pro
290                 295                 300

Leu Asp Ser
305

<210> SEQ ID NO 49
<211> LENGTH: 326
<212> TYPE: PRT
<213> ORGANISM: Homo sapiens

<400> SEQUENCE: 49

Met Pro Asp Asn Arg Gln Pro Arg Asn Arg Gln Pro Arg Ile Arg Ser
1               5                   10                  15

Gly Asn Glu Pro Arg Ser Ala Pro Ala Met Glu Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
50                  55                  60

Gly Cys Glu His Ile Phe Cys Ser Asn Ile Phe Gly Leu Arg Pro Val
65                  70                  75                  80

Asp Tyr Thr Asp Asp Glu Ser Met Lys Ser Leu Leu Leu Leu Pro Glu
                85                  90                  95

Lys Asn Glu Ser Ser Ser Ala Ser His Cys Ser Val Met Asn Thr Gly
            100                 105                 110

Gln Arg Arg Asp Gly Pro Leu Val Leu Ile Gly Ser Gly Leu Ser Ser
        115                 120                 125

Glu Gln Gln Lys Met Leu Ser Glu Leu Ala Val Ile Leu Lys Ala Lys
130                 135                 140

Lys Tyr Thr Glu Phe Asp Ser Thr Val Thr His Val Val Pro Gly
145                 150                 155                 160

Asp Ala Val Gln Ser Thr Leu Lys Cys Met Leu Gly Ile Leu Asn Gly
                165                 170                 175

Cys Trp Ile Leu Lys Phe Glu Trp Val Lys Ala Cys Leu Arg Arg Lys
            180                 185                 190

Val Cys Glu Gln Glu Glu Lys Tyr Glu Ile Pro Glu Gly Pro Arg Arg
        195                 200                 205

Ser Arg Leu Asn Arg Glu Gln Leu Leu Pro Lys Leu Phe Asp Gly Cys
210                 215                 220

Tyr Phe Tyr Leu Trp Gly Thr Phe Lys His His Pro Lys Asp Asn Leu
225                 230                 235                 240

Ile Lys Leu Val Thr Ala Gly Gly Gln Ile Leu Ser Arg Lys Pro
                245                 250                 255

Lys Pro Asp Ser Asp Val Thr Gln Thr Ile Asn Thr Val Ala Tyr His
            260                 265                 270
```

```
Ala Arg Pro Asp Ser Asp Gln Arg Phe Cys Thr Gln Tyr Ile Ile Tyr
        275                 280                 285

Glu Asp Leu Cys Asn Tyr His Pro Glu Arg Val Arg Gln Gly Lys Val
290                 295                 300

Trp Lys Ala Pro Ser Ser Trp Phe Ile Asp Cys Val Met Ser Phe Glu
305                 310                 315                 320

Leu Leu Pro Leu Asp Ser
                325

<210> SEQ ID NO 50
<211> LENGTH: 264
<212> TYPE: PRT
<213> ORGANISM: Homo sapiens

<400> SEQUENCE: 50

Met Pro Asp Asn Arg Gln Pro Arg Asn Arg Gln Pro Arg Ile Arg Ser
1               5                   10                  15

Gly Asn Glu Pro Arg Ser Ala Pro Ala Met Gly Pro Asp Gly Arg Gly
            20                  25                  30

Ala Trp Ala His Ser Arg Ala Ala Leu Asp Arg Leu Glu Lys Leu Leu
        35                  40                  45

Arg Cys Ser Arg Cys Thr Asn Ile Leu Arg Glu Pro Val Cys Leu Gly
    50                  55                  60

Gly Cys Glu His Ile Phe Cys Ser Asn Cys Val Ser Asp Cys Ile Gly
65                  70                  75                  80

Thr Gly Cys Pro Val Cys Tyr Thr Pro Ala Trp Ile Gln Asp Leu Lys
                85                  90                  95

Ile Asn Arg Gln Leu Asp Ser Met Ile Gln Leu Cys Ser Lys Leu Arg
            100                 105                 110

Asn Leu Leu His Asp Asn Glu Leu Ser Gly Val Lys Ala Cys Leu Arg
        115                 120                 125

Arg Lys Val Cys Glu Gln Glu Lys Tyr Glu Ile Pro Glu Gly Pro
    130                 135                 140

Arg Arg Ser Arg Leu Asn Arg Glu Gln Leu Leu Pro Lys Leu Phe Asp
145                 150                 155                 160

Gly Cys Tyr Phe Tyr Leu Trp Gly Thr Phe Lys His His Pro Lys Asp
                165                 170                 175

Asn Leu Ile Lys Leu Val Thr Ala Gly Gly Gln Ile Leu Ser Arg
            180                 185                 190

Lys Pro Lys Pro Asp Ser Asp Val Thr Gln Thr Ile Asn Thr Val Ala
        195                 200                 205

Tyr His Ala Arg Pro Asp Ser Asp Gln Arg Phe Cys Thr Gln Tyr Ile
    210                 215                 220

Ile Tyr Glu Asp Leu Cys Asn Tyr His Pro Glu Arg Val Arg Gln Gly
225                 230                 235                 240

Lys Val Trp Lys Ala Pro Ser Ser Trp Phe Ile Asp Cys Val Met Ser
                245                 250                 255

Phe Glu Leu Leu Pro Leu Asp Ser
            260

<210> SEQ ID NO 51
<211> LENGTH: 167
<212> TYPE: PRT
<213> ORGANISM: Homo sapiens

<400> SEQUENCE: 51
```

```
Met Val Ala Val Pro Gly Pro Thr Val Ala Pro Arg Ser Thr Ala Trp
1               5                   10                  15

Arg Ser Cys Cys Ala Ala Arg Val Gly Val Lys Ala Cys Leu Arg Arg
            20                  25                  30

Lys Val Cys Glu Gln Glu Lys Tyr Glu Ile Pro Glu Gly Pro Arg
        35                  40                  45

Arg Ser Arg Leu Asn Arg Glu Gln Leu Leu Pro Lys Leu Phe Asp Gly
        50                  55                  60

Cys Tyr Phe Tyr Leu Trp Gly Thr Phe Lys His His Pro Lys Asp Asn
65                  70                  75                  80

Leu Ile Lys Leu Val Thr Ala Gly Gly Gly Gln Ile Leu Ser Arg Lys
            85                  90                  95

Pro Lys Pro Asp Ser Asp Val Thr Gln Thr Ile Asn Thr Val Ala Tyr
            100                 105                 110

His Ala Arg Pro Asp Ser Asp Gln Arg Phe Cys Thr Gln Tyr Ile Ile
            115                 120                 125

Tyr Glu Asp Leu Cys Asn Tyr His Pro Glu Arg Val Arg Gln Gly Lys
        130                 135                 140

Val Trp Lys Ala Pro Ser Ser Trp Phe Ile Asp Cys Val Met Ser Phe
145                 150                 155                 160

Glu Leu Leu Pro Leu Asp Ser
                165
```